US008262692B2

(12) United States Patent  
Rudakov

(10) Patent No.: US 8,262,692 B2
(45) Date of Patent: Sep. 11, 2012

(54) ENDOVASCULAR DEVICE

(75) Inventor: Leon Rudakov, San Marcos, CA (US)

(73) Assignee: Merlin MD Pte Ltd, Singapore (SG)

( * ) Notice: Subject to any disclaimer, the term of this patent is extended or adjusted under 35 U.S.C. 154(b) by 951 days.

(21) Appl. No.: 12/205,827

(22) Filed: Sep. 5, 2008

(65) Prior Publication Data

US 2010/0063582 A1    Mar. 11, 2010

(51) Int. Cl.
*A61M 29/00* (2006.01)
*A61B 17/08* (2006.01)

(52) U.S. Cl. .......................... 606/200; 606/213

(58) Field of Classification Search ............... 606/153, 606/191, 200, 213; 623/1.1, 1.13, 1.36, 1.49
See application file for complete search history.

(56) References Cited

U.S. PATENT DOCUMENTS

| | | |
|---|---|---|
| 4,503,569 A | 3/1985 | Dotter |
| 5,041,441 A | 8/1991 | Radin et al. |
| 5,234,457 A | 8/1993 | Anderson |
| 5,356,423 A | 10/1994 | Tihon et al. |
| 5,405,377 A | 4/1995 | Cragg |
| D359,802 S | 6/1995 | Fontaine |
| 5,421,955 A | 6/1995 | Lau et al. |
| 5,443,458 A | 8/1995 | Eury |
| 5,514,154 A | 5/1996 | Lau et al. |
| 5,562,725 A | 10/1996 | Schmitt et al. |
| 5,589,563 A | 12/1996 | Ward et al. |
| 5,601,593 A | 2/1997 | Freitag |
| 5,620,763 A | 4/1997 | House et al. |
| 5,630,840 A | 5/1997 | Mayer |
| 5,632,840 A | 5/1997 | Campbell |
| 5,639,278 A | 6/1997 | Dereume et al. |
| 5,700,285 A | 12/1997 | Myers et al. |
| D390,957 S | 2/1998 | Fontaine |
| 5,718,973 A | 2/1998 | Lewis et al. |

(Continued)

FOREIGN PATENT DOCUMENTS

EP    0754435    1/1997

(Continued)

OTHER PUBLICATIONS

Chatterjee, S., Lactosylceramide Stimulates Aortic Smooth Muscle Cell Proliferation, Biochemical and Biophysical Research Communications, Dec. 16, 1991, pp. 554-561, vol. 181, No. 2., Academic Press, Orlando, FL.

(Continued)

*Primary Examiner* — Julian Woo
(74) *Attorney, Agent, or Firm* — McDermott Will & Emery LLP

(57) ABSTRACT

Embodiments of an endovascular device and of methods for treating an aneurysm therewith are described. In certain embodiments, an endovascular device includes a distal assembly coupled to a flow reducing member. In some embodiments, the distal assembly is composed of multiple engagement members that, when deployed within an aneurysm, engage an inner surface of the aneurysm. In certain embodiments, the engagements members are substantially parallel to a central axis of the distal assembly in a first position and shift away from the central axis to a second position, and the distal ends of some engagement members are substantially curled when in the second position. In certain embodiments, the flow-reducing member reduces blood flow from a blood vessel into the aneurysm. In certain embodiments the flow reducing member includes a membrane, which can include a porous section.

49 Claims, 24 Drawing Sheets

U.S. PATENT DOCUMENTS

| | | | |
|---|---|---|---|
| 5,735,893 A | 4/1998 | Lau et al. |
| 5,744,515 A | 4/1998 | Clapper |
| 5,766,238 A | 6/1998 | Lau et al. |
| 5,769,884 A | 6/1998 | Solovay |
| 5,810,870 A | 9/1998 | Myers et al. |
| 5,843,172 A | 12/1998 | Yan |
| 5,858,556 A | 1/1999 | Eckert et al. |
| 5,866,217 A | 2/1999 | Stenoien et al. |
| 5,902,475 A | 5/1999 | Trozera et al. |
| 5,925,075 A | 7/1999 | Myers et al. |
| 5,948,018 A | 9/1999 | Dereume et al. |
| 5,951,599 A | 9/1999 | McCrory |
| 5,993,489 A | 11/1999 | Lewis et al. |
| 6,001,123 A | 12/1999 | Lau |
| 6,010,530 A | 1/2000 | Goicoechea |
| 6,024,765 A | 2/2000 | Wallace et al. |
| 6,027,811 A | 2/2000 | Campbell et al. |
| 6,033,435 A | 3/2000 | Penn et al. |
| 6,036,720 A | 3/2000 | Abrams et al. |
| 6,056,776 A | 5/2000 | Lau et al. |
| 6,066,167 A | 5/2000 | Lau et al. |
| 6,139,564 A | 10/2000 | Teoh |
| 6,140,127 A | 10/2000 | Sprague |
| 6,168,610 B1 | 1/2001 | Marin et al. |
| 6,174,328 B1 | 1/2001 | Cragg |
| 6,217,607 B1 | 4/2001 | Alt |
| 6,240,616 B1 | 6/2001 | Yan |
| 6,240,948 B1 | 6/2001 | Hansen, III et al. |
| 6,248,190 B1 | 6/2001 | Stinson |
| 6,309,367 B1 | 10/2001 | Boock |
| 6,312,463 B1 | 11/2001 | Rourke et al. |
| 6,315,791 B1 | 11/2001 | Gingras et al. |
| 6,409,754 B1 | 6/2002 | Smith et al. |
| 6,416,474 B1 | 7/2002 | Penner et al. |
| 6,451,050 B1 | 9/2002 | Rudakov et al. |
| 6,451,052 B1 | 9/2002 | Burmeister et al. |
| 6,454,780 B1 | 9/2002 | Wallace |
| 6,485,507 B1 | 11/2002 | Walak et al. |
| 6,488,701 B1 | 12/2002 | Nolting et al. |
| 6,508,832 B1 | 1/2003 | Jalisi et al. |
| 6,517,571 B1 | 2/2003 | Brauker et al. |
| 6,527,802 B1 | 3/2003 | Mayer |
| 6,533,905 B2 | 3/2003 | Johnson et al. |
| 6,547,815 B2 | 4/2003 | Myers |
| 6,582,461 B1 | 6/2003 | Burmeister et al. |
| 6,582,652 B2 | 6/2003 | Craig |
| 6,613,072 B2 | 9/2003 | Lau et al. |
| 6,623,520 B2 | 9/2003 | Jalisi |
| 6,652,574 B1 | 11/2003 | Jayaraman |
| D484,979 S | 1/2004 | Fontaine |
| 6,673,108 B2 | 1/2004 | Zilla et al. |
| 6,676,701 B2 | 1/2004 | Rourke et al. |
| 6,679,910 B1 | 1/2004 | Granada |
| 6,695,833 B1 | 2/2004 | Frantzen |
| 6,695,876 B1 | 2/2004 | Marotta et al. |
| 6,699,276 B2 | 3/2004 | Sogard et al. |
| 6,706,061 B1 | 3/2004 | Fischell et al. |
| 6,719,782 B1 | 4/2004 | Chuter |
| 6,730,108 B2 * | 5/2004 | Van Tassel et al. ............ 606/200 |
| 6,736,844 B1 | 5/2004 | Glatt et al. |
| 6,802,851 B2 | 10/2004 | Jones et al. |
| 6,818,013 B2 | 11/2004 | Mitelberg et al. |
| 6,821,293 B2 | 11/2004 | Pinchasik |
| 6,855,154 B2 | 2/2005 | Abdel-Gawwad |
| 6,899,727 B2 | 5/2005 | Armstrong et al. |
| 6,936,055 B1 | 8/2005 | Ken et al. |
| 6,949,116 B2 | 9/2005 | Solymar et al. |
| 6,979,349 B1 | 12/2005 | Dang et al. |
| 7,029,493 B2 | 4/2006 | Majercak et al. |
| 7,041,129 B2 | 5/2006 | Rourke et al. |
| 7,060,091 B2 | 6/2006 | Killion et al. |
| 7,105,019 B2 | 9/2006 | Hojeibane |
| 7,153,322 B2 | 12/2006 | Alt |
| 7,169,174 B2 | 1/2007 | Fischell et al. |
| D553,746 S | 10/2007 | Fliedner |
| D553,747 S | 10/2007 | Fliedner |
| 7,306,622 B2 | 12/2007 | Jones et al. |
| 7,311,726 B2 | 12/2007 | Mitelberg et al. |
| 7,704,267 B2 * | 4/2010 | Tessmer ........................ 606/200 |
| 2002/0035394 A1 | 3/2002 | Fierens et al. |
| 2002/0042646 A1 | 4/2002 | Wall |
| 2002/0045931 A1 | 4/2002 | Sogard et al. |
| 2002/0049495 A1 | 4/2002 | Kutryk et al. |
| 2002/0065546 A1 | 5/2002 | Machan et al. |
| 2002/0111543 A1 | 8/2002 | Penner et al. |
| 2002/0151968 A1 | 10/2002 | Zilla et al. |
| 2003/0018294 A1 | 1/2003 | Cox |
| 2003/0060782 A1 | 3/2003 | Bose et al. |
| 2003/0093111 A1 | 5/2003 | Ken et al. |
| 2003/0171801 A1 | 9/2003 | Bates |
| 2003/0229286 A1 | 12/2003 | Lenker |
| 2003/0229393 A1 | 12/2003 | Kutryk et al. |
| 2003/0233141 A1 | 12/2003 | Israel |
| 2004/0029268 A1 | 2/2004 | Colb et al. |
| 2004/0087998 A1 | 5/2004 | Lee et al. |
| 2004/0116998 A1 | 6/2004 | Erbel et al. |
| 2004/0170685 A1 | 9/2004 | Carpenter et al. |
| 2004/0172121 A1 | 9/2004 | Eidenschink et al. |
| 2004/0186562 A1 | 9/2004 | Cox |
| 2004/0193206 A1 | 9/2004 | Gerberding et al. |
| 2005/0043787 A1 | 2/2005 | Kutryk et al. |
| 2005/0075716 A1 | 4/2005 | Yan |
| 2005/0096725 A1 | 5/2005 | Pomeranz et al. |
| 2005/0124896 A1 | 6/2005 | Richter et al. |
| 2005/0137677 A1 | 6/2005 | Rush |
| 2005/0137680 A1 | 6/2005 | Ortiz et al. |
| 2005/0154448 A1 | 7/2005 | Cully et al. |
| 2005/0171593 A1 | 8/2005 | Whirley et al. |
| 2005/0267568 A1 | 12/2005 | Berez et al. |
| 2005/0283220 A1 | 12/2005 | Gobran et al. |
| 2006/0020322 A1 | 1/2006 | Leynov et al. |
| 2006/0036311 A1 | 2/2006 | Nakayama et al. |
| 2006/0106421 A1 | 5/2006 | Teoh |
| 2006/0121080 A1 | 6/2006 | Lye et al. |
| 2006/0136037 A1 | 6/2006 | DeBeer et al. |
| 2006/0142849 A1 | 6/2006 | Killion et al. |
| 2006/0149355 A1 | 7/2006 | Mitelberg et al. |
| 2006/0155355 A1 | 7/2006 | Jung |
| 2006/0173530 A1 | 8/2006 | Das |
| 2006/0200230 A1 | 9/2006 | Richter |
| 2006/0200234 A1 | 9/2006 | Hines |
| 2006/0206199 A1 | 9/2006 | Churchwell et al. |
| 2006/0217799 A1 | 9/2006 | Mailander et al. |
| 2006/0224237 A1 | 10/2006 | Furst et al. |
| 2006/0259123 A1 | 11/2006 | Dorn |
| 2006/0265051 A1 | 11/2006 | Caro et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0287710 A1 | 12/2006 | Lendlein et al. |
| 2007/0038288 A1 | 2/2007 | Lye et al. |
| 2007/0083258 A1 | 4/2007 | Falotico et al. |
| 2007/0088387 A1 | 4/2007 | Eskridge et al. |
| 2007/0112415 A1 | 5/2007 | Bartlett |
| 2007/0213800 A1 | 9/2007 | Fierens et al. |
| 2007/0276477 A1 | 11/2007 | Lee et al. |
| 2007/0288083 A1 | 12/2007 | Hines |
| 2008/0004653 A1 | 1/2008 | Sherman et al. |
| 2009/0054966 A1 | 2/2009 | Rudakov et al. |

FOREIGN PATENT DOCUMENTS

| | | |
|---|---|---|
| EP | 0 864 301 | 9/1998 |
| EP | 0947204 | 10/1999 |
| EP | 1121911 | 8/2001 |
| EP | 1 129 666 | 9/2001 |
| EP | 1391184 | 2/2004 |
| EP | 1 470 795 | 10/2004 |
| EP | 1543798 | 6/2005 |
| EP | 1 550 477 | 7/2005 |
| EP | 1797844 | 6/2007 |
| JP | 1 254 623 | 10/1989 |
| WO | WO 98/14137 | 4/1998 |
| WO | WO 99-02092 | 1/1999 |
| WO | WO 99-58084 | 11/1999 |
| WO | WO 99-62432 | 12/1999 |
| WO | WO 00/01308 | 1/2000 |
| WO | WO 00-06145 | 2/2000 |

| | | |
|---|---|---|
| WO | WO 00-47134 | 8/2000 |
| WO | WO 00-51522 | 9/2000 |
| WO | WO 00-56247 | 9/2000 |
| WO | WO 01/03607 | 1/2001 |
| WO | WO 01/66167 | 9/2001 |
| WO | WO 01-87184 | 11/2001 |
| WO | WO 01-93782 | 12/2001 |
| WO | WO 02-22024 | 3/2002 |
| WO | WO 02-051336 | 7/2002 |
| WO | WO 02/069783 | 9/2002 |
| WO | WO 02/078764 | 10/2002 |
| WO | WO 03-049600 | 6/2003 |
| WO | WO 03-065881 | 8/2003 |
| WO | WO 04-000379 | 12/2003 |
| WO | WO 2004-028405 | 4/2004 |
| WO | WO 2005/000165 | 1/2005 |
| WO | WO 2005-065580 | 7/2005 |
| WO | WO 2005-086831 | 9/2005 |
| WO | WO 2005-094725 | 10/2005 |
| WO | WO 2005-094726 | 10/2005 |
| WO | WO 2006-033641 | 3/2006 |

OTHER PUBLICATIONS

Reul, J. et al., Long-Term Angiographic and Histopathalogic Findings in Experimental Aneurysms of the Carotid Bifurcation Embolized with Platinum and Tungsten Colis, American Journal of Neuroradiology, Jan. 1997, pp. 35-42, vol. 18.

* cited by examiner

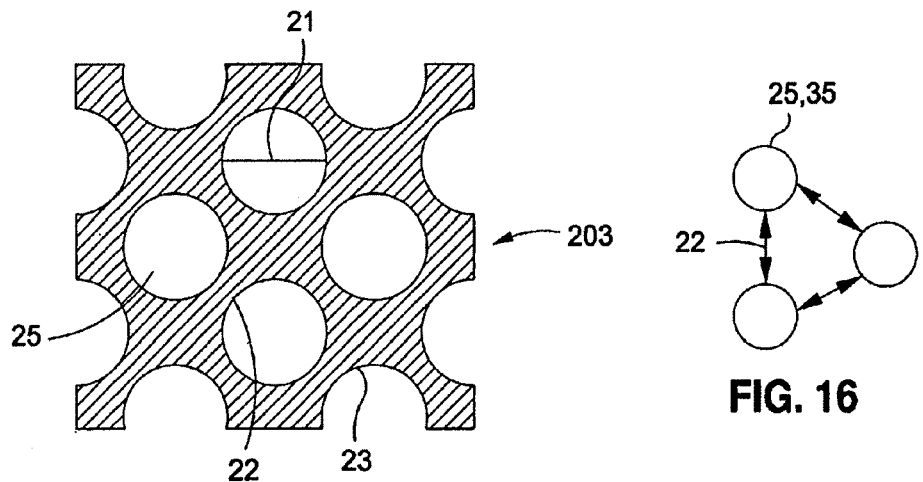
FIG. 15
FIG. 16
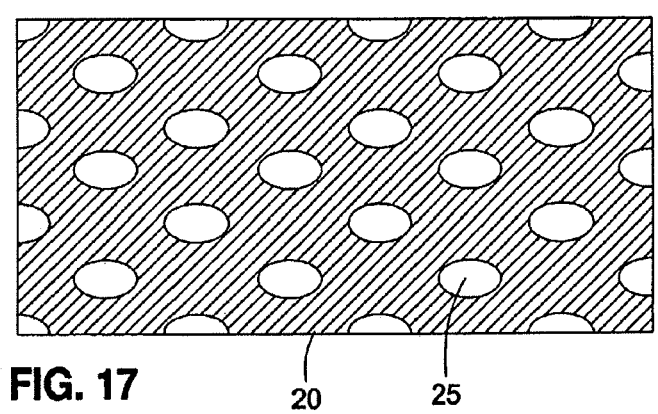
FIG. 17
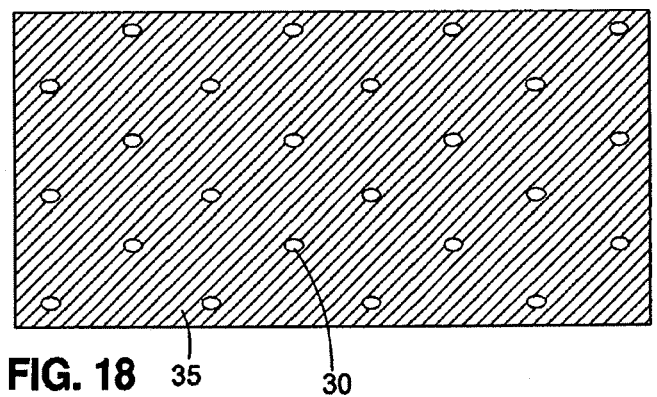
FIG. 18

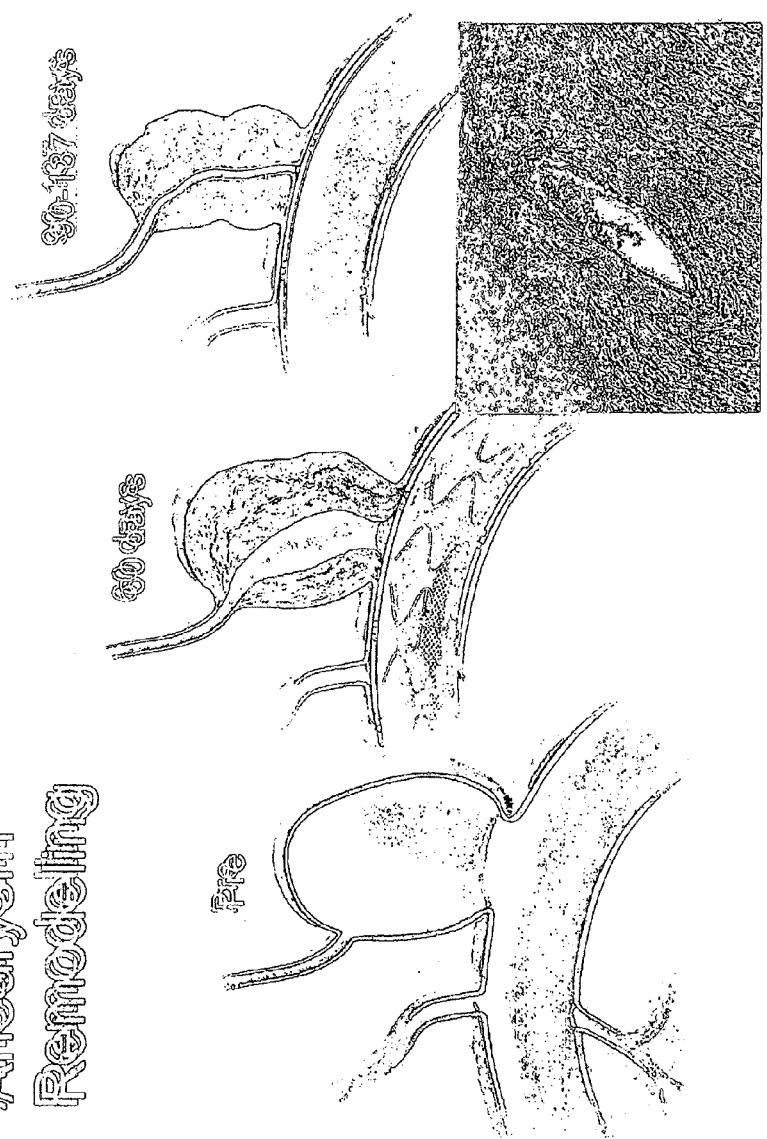

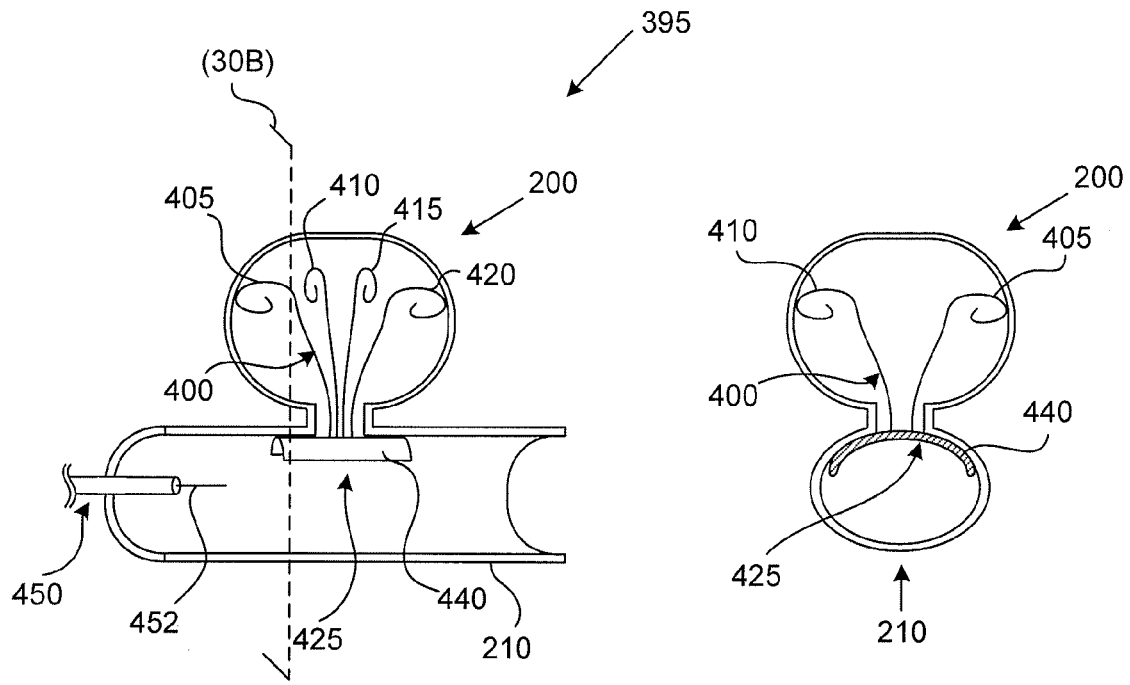
FIG. 30A  FIG. 30B
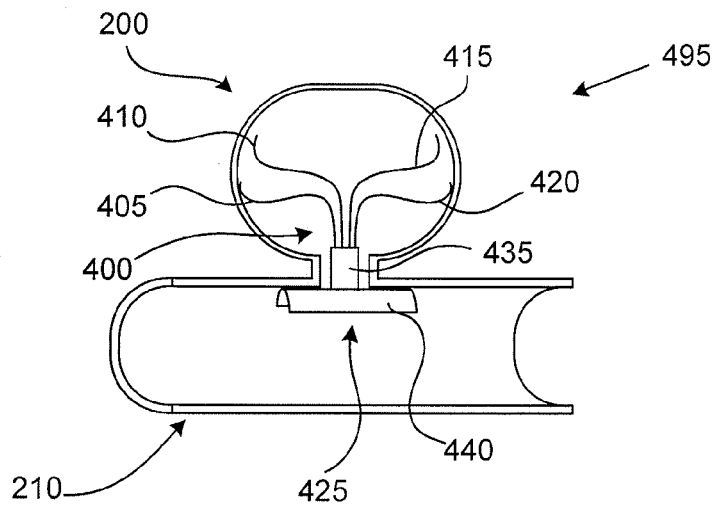
FIG. 31

ENDOVASCULAR DEVICE

FIELD OF THE INVENTION

The invention concerns an endovascular device for insertion into a bodily vessel to treat a diseased, damaged, or weakened portion of a vessel.

BACKGROUND OF THE INVENTION

Vascular diseases include aneurysms causing hemorrhage, atherosclerosis causing occlusion of blood vessels, vascular malformation, and tumors. Vessel occlusion or rupture of an aneurysm within the brain can result in stroke. Aneurysms fed by intracranial arteries can grow within the brain to a point where their size can also cause a stroke or the symptoms of a stroke, requiring surgery to remove the aneurysm, or other remedial intervention.

Occlusion of coronary arteries is a common cause of heart attack. Diseased and obstructed coronary arteries result in restricted blood flow in the heart which can lead to ischemia or necrosis. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Conventional open-heart surgery is of course highly invasive and traumatic for patients undergoing such procedures. Therefore, less invasive procedures that accomplish the same goals are highly desirable.

One alternative method of treatment involves the use of balloon angioplasty as a way in which to reopen the lumen of an occluded vessel. In this procedure a folded balloon is inserted via a catheter into a stenosed region that is either partially or fully occluding the vessel lumen. Inflation of the balloon physically expands the lumen, reopening the occluded region, and restoring normal or at least significantly improved blood flow through the vessel. Alternatively, occlusive atheromas may be cut from the inner surface, a procedure known as atherectomy. In both methods, a certain incidence of restenosis (resealing) occurs resulting in a loss of the benefit of the procedure, and potentially the need for additional rounds of therapy. Restenosis also results in reversion back to the original occluded condition, such that the vessel no longer conducts a normal flow volume, which can lead to ischemia or infarct depending on the particular location and function of the vessel in question.

A recent preferred therapy for repairing vascular occlusions involves placement of an expandable metal wire-frame (i.e. a stent) within the occluded region of a blood vessel in order to keep the lumen of the vessel open. Stents are generally delivered to the desired location within a vascular system by an intraluminal route, usually via a catheter. Advantages of the stent placement method over conventional vascular surgery include obviating the need for surgically exposing, removing, replacing, or by-passing the defective blood vessel, including heart-lung bypass, opening the chest and in some cases general anaesthesia.

When inserted and deployed in a vessel, duct or tract (all of which can be conveniently referred to as a vessel) of the body, for example, a coronary artery after dilation of the artery by balloon angioplasty, a stent acts as a prosthesis to maintain the vessel in an open state, thus providing a fluid pathway in the previously occluded vessel. The stent usually has an open-ended tubular form with interconnected struts as its sidewall to enable its expansion from a first outside diameter which is sufficiently small to allow the stent to traverse the vessel lumen and be delivered to a site where it is to be deployed, then expanded to a second outside diameter sufficiently large to engage the inner lining of the vessel for retention at that site. The stent may be expanded via the use of a mechanical device, for example a pressurizable balloon, or alternatively the stent may be self-expanding. Self-expanding stents can be manufactured at a to be deployed size, and then compressed to a smaller size to enable delivery, or may be manufactured from shape memory materials that are deformable to a memorized shape in response to an externally applied energy.

Usually a stent suitable for successful interventional placement should be hypoallergenic, or preferably non-allergenic, have good radio-opacity to permit radiographic visualization, free from distortion during magnetic resonance imaging (MRI), plastically deformable, resistant to vessel recoil, and be as thin as possible to minimize obstruction to blood flow (or other materials or fluids in vessels other than those of the cardiovascular system), and be relatively non-reactive in terms of eliciting thrombogenic responses.

The typical reaction when a foreign body is implanted in a body vessel is generally negative. Foreign bodies frequently cause an inflammatory response, and in the case of blood vessels, neointimal proliferation which results in narrowing and occlusion of the body vessel, obviating the benefit of the implant. As a result, both selection of the materials from which the stent is composed, as well as the design of the stent, play an important role in influencing the final suitability of the device in practice. Therefore, in addition to the structural requirements for a stent to maintain a previously occluded vessel in a substantially open conformation, stents must also be biologically compatible, and must be chemically stable when exposed to a biological environment.

A variety of materials have been tested and used in stents to address the issues of biocompatibility and material stability. For example, polyurethanes have been used in long term implants, but are not always suitable for use in endovascular treatments, especially in small blood vessels. Small blood vessels are considered to be those with an inner diameter of 2.0 to 5.0 mm. In addition, many commercially available polymers are with additives, or have impurities, that are surface-active and so reduce their usefulness in some biological applications.

More recently, polymers have been developed which can be further modified by the covalent attachment of various surface-modifying end groups, these end groups reducing the reactivity of the material with cells and other factors that function in the immune response. End groups can also be useful in providing greater chemical stability to the material, reducing degradation and improving the longevity of the prosthesis. For example, U.S. Pat. No. 5,589,563 (Ward & White) discloses a series of biomedical base polymers with covalently attached end groups that give the polymer certain desirable properties. These modified polymers possess surface properties that improve the biocompatibility and overall performance of objects fashioned from them.

In addition to their biomechanical functionality, implantable medical devices like stents have been utilized for delivery of drugs or bioreagents for different biological applications. U.S. Pat. No. 5,891,108 (Leone et al.) discloses a hollow tubular wire stent with holes through which an active substance can be delivered to a site in a vessel. In some cases the drugs or bioreagents can be coated directly onto the surface of the implantable medical devices or mixed with polymeric materials that are then applied to the surface of the devices. For example, U.S. Pat. No. 5,599,352 (Dinh et al.) discloses a drug eluting stent comprising a stent body, a layer of a composite of a polymer combined with a therapeutic substance, overlaid by a second layer comprising fibrin.

However, each of these methods suffers from one or more problems including poor control of release or limitations of the form of drug or other reagent that can be applied. Also, these methods are unsuitable for situations where it would be desirable to maintain the bioactive molecule on the device rather than having it be released, in order to maintain a relatively high local activity of the reagent of interest.

As a result, in practice, the design and use of stents in the repair of aneurysms or other vessel defects or diseases typically represents a compromise among competing factors. First, the stent must adequately support the diseased or weakened region in order to prevent rupture of the aneurysm or vessel during and after stent placement, either of which could lead to serious complications including death, depending on the size, location and nature of the aneurysm or defect. Second, in the case of stents use in the repair of aneurysms, the stent must permit sufficient blood supply to maintain the patency of both the parent and perforator vessels, while at the same time limiting flow to the aneurysm proper. Generally speaking, flow of material through the framework of a stent is achieved by regulating the porosity of the stent.

Stent porosity can be managed in a number of ways. The simplest way is to manufacture the stent so that the framework itself defines the porosity of the device. However, in biological applications, regulating movement of materials on cellular or subcellular scale is required, and it is difficult and costly to manufacture stents that have such fine effective pore size. Other approaches have been to cover the stent framework for example with a membrane, where the membrane is either impermeable or porous as desired. U.S. Patent Application No. 2006/0217799 (Mailander et al.) discloses a stent comprising a grid or mesh structure in which one or more cells of the grid are covered with a membrane. Similarly, U.S. Patent Application No. 2006/0200230 (Richter) discloses a covering for an endoprosthetic device that comprises a sheath with holes of varying size and varying frequency disposed in different areas of the sheath.

However, a problem inherent with these designs is that they are not easily adapted for effecting vessel wall repairs where the area of disease, damage or weakness can vary in size. Thus, in order to optimally treat an aneurysm, it would be necessary to tailor the stent and its covering to more or less the precise size of the damaged area, in order to properly occlude the aneurysm site, while maintaining vessel patency in the parent vessel and any perforator vessels. Furthermore, these designs are not optimized such that they will generally provide flow to perforator vessels that are part of the collateral circulation in the area of the diseased, damaged, or weakened vessel, while blocking flow to an aneurysm.

SUMMARY OF THE INVENTION

Some embodiments of the present invention provide an endovascular device, for treating an aneurysm of a body vessel, comprising a distal assembly, movable from a first position to a second position when the distal assembly is at least partially in an aneurysm; and a first flow-reducing member, coupled to the distal assembly, that reduces blood flow from the body vessel into the aneurysm when the distal assembly is in the second position; wherein the distal assembly comprises a plurality of engagement members, each of which extends, from a proximal portion to a distal portion, away from the flow-reducing member, and, when the distal assembly is in the first position, each of the plurality of engagement members is substantially parallel to a central axis of the distal assembly, and, when the distal assembly changes from the first to the second position, the distal portion of each of the plurality of engagement members moves away from the central axis, such that the distal portions of each of the plurality of engagement members: substantially curl; move closer to the first flow-reducing member; and engage an inner surface of the aneurysm.

In certain embodiments, an endovascular device of the invention comprises a mass and/or a volume less than a mass and/or a volume of known aneurysm "coil" devices, which provides such an endovascular device of the present invention with surprisingly improved properties in regard to aneurismal mass effects, in regard to pressure effects on nerve tissue at or near the aneurysm deployment site, and in regard to allowing for aneurysmal shrinkage over time. In certain embodiments, an endovascular device of the invention comprises a flow reducing member that resides entirely within the aneurysm and has no impact on branch vessels in a proximity of the aneurysm.

As used herein, the term "curl" encompasses forming a linear element into a curved two-dimensional or three-dimensional shape, or a curved element into a shape having a different curvature. The term "curl" also includes bending a structure such as a structure having a joint. The "curl" or bend can be at the joint or elsewhere in the structure.

In some embodiments, at least one of the plurality of engagement members comprises a polymer. In some embodiments, the polymer comprises at least one member selected from the group consisting of polyurethane, polyethylene terephthalate, expanded polytetrafluoroethylene (ePTFE), polyvinylchloride, nylon, polyimide, polyurethane ether, polyurethane ester, polyurethaneurea, polylactide, polyglycolide, poly-orthoester, polyphosphazene, polyanhydride, and polyphosphoester.

In some embodiments, at least one of the plurality of engagement members comprises a metal. In some embodiments, the metal comprises at least one member selected from the group consisting of NiTi, tungsten, stainless steel, iridium, platinum, alloys and/or joined combinations thereof.

In some embodiments, a distal end of at least one of the plurality of engagement members is blunt.

In some embodiments, when the distal assembly is in the second position, a distal end of each of the plurality of engagement members engages the inner surface of the aneurysm.

In some embodiments, when the distal assembly is in the second position, the first flow-reducing member resides in the body vessel.

In some embodiments, when the distal assembly is in the second position, the first flow-reducing member resides in the aneurysm.

In some embodiments, an endovascular device comprises a second flow-reducing member, coupled to the first flow-reducing member or to the distal assembly.

In some embodiments, the distal assembly is in the second position, the first flow-reducing member resides in the body vessel and the second flow-reducing member resides in the aneurysm.

In some embodiments, an endovascular device comprises a linking member that couples the second flow-reducing member to the first flow-reducing member or to the distal assembly.

In some embodiments, at least one of the linking member, the distal assembly, the first flow-reducing member, and the second flow-reducing member comprises a metal.

In some embodiments, at least one of the linking member, the distal assembly, the first flow-reducing member, and the second flow-reducing member comprises at least one metal selected from the group consisting of NiTi, tungsten, stainless steel, iridium, and platinum.

In some embodiments, the linking member comprises a wire.

In some embodiments, each of the linking member, the first flow-reducing member, the second flow-reducing member, and the distal assembly comprises a metal, and wherein a weld couples the linking member to at least one of the distal assembly, the first flow-reducing member, and the second flow-reducing member.

In some embodiments, the second flow-reducing member comprises a plug that substantially resides within a neck of the aneurysm and substantially inhibits blood flow through the neck.

In some embodiments, the first flow-reducing member comprises a membrane.

In some embodiments, when the distal assembly is in the second position within the aneurysm, a thickness of the membrane is between about 5 µm and about 500 µm.

In some embodiments, the membrane comprises at least one polymer selected from the group consisting of ePTFE, polyurethane, polyethylene terephthalate, polyvinylchloride, nylon, polyimide, silicone, polyurethane ether, polyurethane ester, polyurethaneura, polylactide, polyglycolide, polyorthoester, polyphosphazene, polyanhydride, and polyphosphoester.

In some embodiments, the first flow-reducing member is coupled to the distal assembly by suture or by interweaving.

In some embodiments, at least a portion of the membrane is non-porous.

In some embodiments, the membrane comprises a porous section having a porosity over a length extending from a proximal end of the porous section to a distal end of the porous section, wherein a pore spacing and a pore size of the porous section determine the porosity of the porous section, and wherein, when the distal assembly is in the second position, the membrane is effective to reduce blood flow into the aneurysm and to promote thrombosis at or in the aneurysm.

In some embodiments, a membrane porosity is selected such that, when the distal assembly is in the second position, the porous section of the membrane is effective to enhance endothelial cell migration and tissue growth onto the membrane and to substantially inhibit blood flow from the body vessel into the aneurysm.

In some embodiments, the pore size is between about 1 µm and about 150 µm. In some embodiments, the pore size is between about 10 µm and about 50 µm.

In some embodiments, the pore spacing is between about 40 µm and about 100 µm. In some embodiments, the pore spacing is between about 60 µm and about 75 µm.

In some embodiments, a material ratio of the porous section of the membrane comprises a ratio of a total area of an outer surface of the porous section of the membrane that comprises material to a total area of an outer surface of the porous section that comprises pores.

In some embodiments, when the distal assembly is in the second position, the material ratio is between about 25% and about 90%. In some embodiments, when the distal assembly is in the second position, the material ratio is between about 70% and about 80%. In some embodiments, when the distal assembly is in the second position within the aneurysm, the material ratio is about 75%.

In some embodiments, an endovascular device comprises at least one surface-modifying end group that, when the distal assembly is in the second position, promotes healing of the body vessel. In some embodiments, the at least one surface-modifying end group comprises at least one of a fluorocarbon and the combination of polyethylene glycol and silicon.

In some embodiments, an endovascular device comprises at least one agent, permanently attached to the membrane, that promotes healing of the aneurysm. In some embodiments, the healing agent comprises at least one of a peptide, a protein, an enzyme regulator, an antibody, a nucleic acid, and a polynucleotide. In some embodiments, an endovascular device comprises an endothelial cell inhibiting agent, such as L-PDMP. In some embodiments, an endovascular device comprises an endothelial cell inducing agent, such as D-PDMP.

Some embodiments of the present invention provide an endovascular device, for treating an aneurysm of a body vessel, comprising means for engaging an inner surface of an aneurysm, the means for engaging being movable from a first position to a second position when the means for engaging is at least partially within an aneurysm; and a first means for reducing blood flow into the aneurysm, the means for reducing blood flow coupled to the means for engaging such that, when the means for engaging is in the second position, the first means for reducing blood flow is effective to reduce blood flow from the body vessel into the aneurysm; wherein the means for engaging comprises a plurality of engagement members, each of which extends, from a proximal portion to a distal portion, away from the flow-reducing member, and wherein, when the means for engaging is in the first position, each of the plurality of engagement members is substantially parallel to a central axis of the distal assembly, and wherein, when the means for engaging changes from the first to the second position, the distal portion of each of the plurality of engagement members moves away from the central axis, such that the distal portions of each of the plurality of engagement members: substantially curl; move closer to the first flow-reducing member; and engage an inner surface of the aneurysm.

In some embodiments, an endovascular device comprises a second means for reducing blood flow into the aneurysm, coupled to the first flow-reducing member and effective to reduce blood flow into the aneurysm when the means for engaging is in the second position. In some embodiments, when the means for engaging is in the second position, the first flow-reducing means resides in the body vessel and the second flow-reducing means resides in the aneurysm.

Some embodiments of the present invention provide a method of treating an aneurysm of a body vessel comprising providing an endovascular device comprising a distal assembly, movable from a first position to a second position when the distal assembly is at least partially within an aneurysm, the distal assembly comprising a plurality of engagement members, each of which extends, from a proximal portion to a distal portion, away from the flow-reducing member and each of which, when the distal assembly is in the first position, is substantially parallel to a central axis of the distal assembly; and a first flow-reducing member, coupled to the distal assembly, that reduces blood flow from the body vessel into the aneurysm when the distal assembly is in the second position; positioning the distal assembly at least partially within the aneurysm; and changing the distal assembly from the first position to the second position such that the distal portion of each of the plurality of engagement members moves away from the central axis, whereby the distal portions of each of the plurality of engagement members: substantially curl; move closer to the first flow-reducing member; and engage an inner surface of the aneurysm.

Some embodiments of the present invention provide an endovascular device, for treating an aneurysm of a body vessel, comprising: a distal assembly, comprising an engagement member, the distal assembly being movable from a first position to a second position when the distal assembly is at least partially in the aneurysm; a flow-reducing assembly, coupled to the distal assembly and comprising a first flow-reducing member, the flow-reducing assembly reducing blood flow from the body vessel into the aneurysm when the distal assembly is in the second position; wherein the engagement member is elongate and curvilinear and extends, from a proximal to a distal end of the engagement member, along a path that originates from a point at the flow-reducing assembly and terminates at a point within the aneurysm when the first flow-reducing member resides in the body vessel; wherein the engagement member is coterminous with the path; wherein, when the distal assembly is in the second position in the aneurysm, the first flow-reducing member resides in the body vessel, a first portion of the engagement member engages a first region of an inner surface of the aneurysm, and a second portion of the engagement member engages a second region of the inner surface of the aneurysm; wherein the first and second regions are spaced at least 2 mm apart. In some embodiments, the flow-reducing assembly further comprises a second flow-reducing member; wherein, when the second flow-reducing member resides at least partially in the aneurysm, and the distal assembly is in the second position, the first flow-reducing member resides in the body vessel.

In some embodiments, a form of an engagement member comprises a curve. In some embodiments, a form of at least a portion of the engagement member is helical.

In some embodiments, the first and the second regions of the inner surface of the aneurysm are spaced at least 4 mm apart. In some embodiments, the first and second portions of the engagement member are spaced at least 2 mm apart. In some embodiments, the first portion and the second portion of the engagement member are spaced at least 4 mm apart.

Some embodiments of the present invention provide an endovascular device for insertion into a body vessel to treat an aneurysmal portion of the body vessel, the endovascular device comprises: an expandable member, expandable from a first position to a second position, said expandable member being expandable radially outwardly to the second position such that an outer surface of said expandable member engages with an inner surface of the vessel so as to maintain a fluid pathway in said vessel through a lumen in the expandable member; a membrane covering at least a portion of an outer surface of said expandable member; a plurality of pores in a porous section of the membrane, the porous section having a substantially uniform porosity over a length extending from a proximal end to a distal end of the porous section, porosity being determined by a pore spacing and a pore size; wherein the proportion of the total area of an outer surface of the porous section that consists of membrane material defines a material ratio; wherein the substantially uniform porosity is selected such that, when the expandable member is positioned in the body vessel, the membrane permits a flow of blood from within the lumen of the expandable member, through at least one of the pores, and into at least one branch vessel that branches off of the body vessel; and wherein the substantially uniform porosity is further selected such that, when the expandable member is positioned in the body vessel, the membrane reduces blood flow to the aneurysmal portion of the vessel, promoting thrombosis at or in the aneurysmal portion.

In some embodiments, the porosity of the porous section is selected such that it enables enhanced endothelial cell migration and tissue in-growth for endothelialization of the neck bridge while substantially preventing blood circulation to the diseased, damaged or weakened portion of the vessel wall.

In some embodiments, an endovascular device of the invention deployed within an aneurysm can be supported in that position by an endovascular device deployed in a body vessel at or near the aneurysm.

In some embodiments, the pore size is between about 1 µm and about 150 µm.

In some embodiments, the pore size is between about 10 µm and about 50 µm.

In some embodiments, the pore spacing is between about 40 µm and about 100 µm.

In some embodiments, the pore spacing is between about 60 µm and about 75 µm.

In some embodiments, the material ratio in an as-manufactured state is between about 85% and about 96%.

In some embodiments, the material ratio in a deployed state is between about 25% and about 90%.

In some embodiments, the material ratio in the deployed state is between about 70% and about 80%.

In some embodiments, the material ratio in the deployed state is about 75%.

In some embodiments, a diameter of the device in the deployed state is between about 2 mm and about 5 mm.

In some embodiments, a thickness of the membrane is between about 25 µm to about 125 µm.

In some embodiments, the thickness of the membrane is measured in an as-manufactured state.

In some embodiments, a thickness of the membrane is between about 5 µm to about 25 µm.

In some embodiments, the thickness of the membrane is measured in a deployed state.

In some embodiments, the device further comprises at least one surface-modifying end group that promotes healing of the body vessel after the device is inserted into the body vessel.

In some embodiments, the surface-modifying end group comprises at least one of a fluorocarbon and the combination of polyethylene glycol and silicon.

In some embodiments, the device further comprises at least one agent, permanently attached the membrane, that promotes healing of the aneurysm.

In some embodiments, at least one permanently attached agent comprises at least one of a peptide, a protein, an enzyme regulator, an antibody, a naturally occurring molecule, a synthetic molecule, a nucleic acid, a polynucleotide, L-PDMP, and D-PDMP.

In some embodiments, each pore has a diameter between about 30 µm and about 40 µm, and a distance between adjacent pores is between about 60 µm and about 70 µm.

In some embodiments, the aneurysmal portion of the vessel is located at or near at least one of an intracranial aneurysm, a saccular aneurysm, a wide-neck aneurysm, a fusiform aneurysm, a caroticocavemous fistula, an arteriovenous malformation, a carotid artery stenosis, a saphenous vein graft, a small vessel stenosis, and a renal artery repair.

In some embodiments, the porous section can be divided into n porous regions, and wherein an outer surface area of each of the n porous regions is substantially 1/n of a total outer surface area of the porous segment, and wherein each one of the n porous regions has substantially the same porosity as each of the other n−1 porous regions.

In some embodiments, n=2.

In some embodiments, n=3.

In some embodiments, n=4.

In some embodiments, n=5.

In some embodiments, the pore size is in a range between about 1 μm and about 150 μm, and pore spacing is between about 10 μm and about 50 μm.

In some embodiments, the pore size is between about 10 μm and about 50 μm, and the pore spacing is between about 60 μm and about 75 μm.

In some embodiments, an endovascular device system for insertion into a body vessel to treat an aneurysmal portion of the vessel, the endovascular device comprises: an expandable member, expandable from a first position to a second position, said expandable member being expandable radially outwardly to the second position such that an outer surface of said expandable member engages with an inner surface of the vessel so as to maintain a fluid pathway in said vessel through a lumen in the expandable member; a membrane covering at least a portion of an outer surface of said expandable member; a plurality of pores in a porous section of the membrane, the porous section having a substantially uniform porosity over a length extending from a proximal end to a distal end of the porous section, porosity being determined by a pore spacing and a pore size; wherein the proportion of the total area of an outer surface of the porous section that consists of membrane material defines a material ratio; wherein the substantially uniform porosity is selected such that, when the expandable member is positioned in the body vessel, the membrane permits a flow of blood from within the lumen of the expandable member, through at least one of the pores, and into at least one branch vessel that branches off of the body vessel; and wherein the substantially uniform porosity is further selected such that, when the expandable member is positioned in the body vessel, the membrane reduces blood flow to the aneurysmal portion of the vessel, promoting thrombosis at or in the aneurysmal portion; and a delivery device, operable to deliver the expandable member to the aneurysmal portion of the vessel, onto which the expandable member is loaded prior to delivery.

In some embodiments, the pore size is between about 1 μm and about 150 μm.

In some embodiments, the pore size is between about 10 μm and about 50 μm.

In some embodiments, the pore spacing is between about 40 μm and about 100 μm.

In some embodiments, the pore spacing is between about 60 μm and about 75 μm.

In some embodiments, the material ratio in an as-manufactured state is between about 85% and about 96%.

In some embodiments, the material ratio in a deployed state is between about 25% and about 80%.

In some embodiments, the material ratio in the deployed state is between about 70% and about 80%.

In some embodiments, the material ratio in the deployed state is about 75%.

In some embodiments, a diameter of the expandable member in the deployed state is between about 2 mm and about 5 mm In some embodiments, a thickness of the membrane is between about 25 μm to about 125 μm.

In some embodiments, the thickness of the membrane is measured in an as-manufactured state.

In some embodiments, a thickness of the membrane is between about 5 μm to about 25 μm.

In some embodiments, the thickness of the membrane is measured in a deployed state.

In some embodiments, the system further comprises at least one surface-modifying end group that promotes healing of the body vessel after the device is inserted into the body vessel.

In some embodiments, the at least one surface-modifying end group is at least one of a fluorocarbon and the combination of polyethylene glycol and silicon.

In some embodiments, the system further comprises at least one permanently attached agent to promote healing of the aneurysmal portion.

In some embodiments, the at least one permanently attached agent comprises at least one of a peptide, a protein, an enzyme regulator, an antibody, a naturally occurring molecule, a synthetic molecule, a nucleic acid, a polynucleotide, L-PDMP, and D-PDMP.

In some embodiments, each pore has a diameter between about 10 μm and about 50 μm and the distance between adjacent pores is between about 60 μm and about 75 μm.

In some embodiments, the aneurysmal portion of the body vessel is located at or near at least one of an intracranial aneurysm, a saccular aneurysm, a wide-neck aneurysm, a fusiform aneurysm, a caroticocavernous fistula, an arteriovenous malformation, a carotid artery stenosis, a saphenous vein graft, a small vessel stenosis, and a renal artery repair.

In some embodiments, an endovascular device for insertion into a body vessel to treat an aneurysmal portion of a body vessel, the endovascular device comprises: means for maintaining a fluid pathway in the body vessel; means for covering at least part of the means for maintaining, the means for covering having a substantially uniform porosity in a porous segment of the means for covering; and wherein, when the means for maintaining is positioned in a body vessel, the means for covering permits blood flow from the fluid pathway to at least one branch vessel branching off the body vessel, while reducing blood flow to the aneurysmal portion, and the means for maintaining supports the body vessel in the region of the aneurysmal portion and provides a fluid pathway in the body vessel.

In some embodiments, a method of treating a body vessel having an aneurysmal portion comprises the steps of: providing an endovascular device, comprising: an expandable member, expandable from a first position to a second position, said expandable member being expandable radially outwardly to the second position such that an outer surface of said expandable member engages with an inner surface of the body vessel so as to maintain a fluid pathway in said body vessel through a lumen in the expandable member; a membrane covering at least a portion of an outer surface of said expandable member; a plurality of pores in a porous section of the membrane, the porous section having a substantially uniform porosity over a length extending from a proximal end to a distal end of the porous section, porosity being determined by a pore spacing and a pore size; wherein the proportion of the total area of an outer surface of the porous section that consists of membrane material defines a material ratio; wherein the substantially uniform porosity is selected such that, when the expandable member is positioned in the body vessel, the membrane permits a flow of blood from within the lumen of the expandable member, through at least one of the pores, and into at least one branch vessel that branches off of the body vessel; and wherein the substantially uniform porosity is further selected such that, when the expandable member is positioned in the body vessel, the membrane reduces blood flow to the aneurysmal portion of the body vessel, promoting thrombosis at or in the aneurysmal portion; and positioning the expandable member in the body vessel.

In some embodiments, the porosity of the membrane is selected such that it enhances endothelial cell migration and tissue in-growth.

In some embodiments, the pore size is between about 1 μm and about 150 μm.

In some embodiments, the pore size is between about 10 µm and about 50 µm.

In some embodiments, the pore spacing is between about 40 µm and about 100 µm.

In some embodiments, the pore spacing is between about 60 µm and about 75 µm.

In some embodiments, the material ratio in an as manufactured state is between about 85% and about 96%.

In some embodiments, the material ratio in a deployed state is between about 25% and about 80%.

In some embodiments, the material ratio in the deployed state is between about 70% and about 80%.

In some embodiments, the material ratio in the deployed state is about 75%.

In some embodiments, a diameter of the expandable member in the deployed state is between about 2 mm and about 5 mm.

In some embodiments, a thickness of the membrane is between about 25 µm to about 125 µm in the as-manufactured state.

In some embodiments, a thickness of the membrane is between about 5 µm to about 25 µm in the deployed state.

In some embodiments, the method further comprises providing a membrane having at least one surface-modifying end group that encourages healing of the body vessel after the device is inserted.

In some embodiments, the at least one surface-modifying end group is at least one of a fluorocarbon and the combination of polyethylene glycol and silicon.

In some embodiments, the membrane further comprises at least one permanently attached agent to promote healing of the aneurysm.

In some embodiments, the at least one permanently attached agent comprises at least one of a peptide, a protein, an enzyme regulator, an antibody, a naturally occurring molecule, a synthetic molecule, a nucleic acid, a polynucleotide, L-PDMP, and D-PDMP.

An endovascular device, for treating an aneurysm of a body vessel, comprising: a distal assembly comprising an engagement member, the distal assembly being movable from a first position to a second position when the distal assembly is at least partially in an aneurysm; a flow-reducing assembly comprising a first flow-reducing member and coupled to the distal assembly, the flow-reducing assembly reduces blood flow from the body vessel into the aneurysm when the distal assembly is in the second position; wherein the engagement member comprises an elongate and curvilinear form which follows a path originating from a point on the flow-reducing assembly and terminating at a point within the aneurysm; wherein the engagement member is coterminous with the path; wherein a space exists between the origination and termination points of the path; wherein, when the distal assembly is in the second position in the aneurysm, the first flow-reducing member resides in the body vessel, a first portion of the engagement member engages a first region of an inner surface of the aneurysm, and a second portion of the engagement member engages a second region of the inner surface of the aneurysm; wherein the first and second regions are spaced at least 2 mm apart.

In some embodiments, the flow-reducing assembly further comprises a second flow-reducing member, the first flow-reducing member resides in the aneurysm, and the second flow-reducing member resides in the body vessel.

In some embodiments, at least a portion of the form of the engagement member is helical.

In some embodiments, the first and the second regions of the engagement member are spaced at least 4 mm apart In some embodiments, the first and the second portions of the engagement member are spaced at least 2 mm apart.

In some embodiments, the first portion and the second portions of the engagement member are spaced at least 4 mm apart.

In certain embodiments, an endovascular device of the invention that is positionable within an aneurysm can be used to treat a bifurcation aneurysm or a trifurcation aneurysm.

In certain embodiments, an endovascular device positionable within an aneurysm comprises a profile of about 0.018" to about 0.030" and may be delivered by microcatheter as a single unit. Delivery may comprise initial advancement and deployment followed by one or more retraction and repositioning events, if needed. In contrast, known coils are deployed by multiple delivery procedures and lack means for retraction and repositioning after being deployed.

BRIEF DESCRIPTION OF THE DRAWINGS

Examples of embodiments of the invention will now be described with reference to the following drawings.

FIG. 15 illustrate one embodiments of a membrane showing pore positioning.

FIG. 16 illustrates equidistantly spaced pores.

FIG. 17 illustrates a macroporous membrane.

FIG. 18 illustrates a microporous membrane.

FIG. 22 diagrams progressive remodeling of an aneurysm after implantation of a stent.

FIG. 30a illustrates an embodiment of a deployed endoprosthetic aneurysm occlusion device comprising a distal assembly, engagement members, and a flow-reducing member residing in a vessel, and a catheter useful for delivering the device to the aneurysm.

FIG. 30b illustrates a cross section view of the embodiment of the device shown in FIG. 30a.

FIG. 31 illustrates an embodiment of a deployed device comprising a distal assembly, engagement members, a flow-reducing member residing in the vessel, and a linking member.

DETAILED DESCRIPTION OF THE INVENTION

Implantable medical devices include physical structures for delivering drugs or reagents to desired sites within the endovascular system of a human body. These devices may take up diversified shapes and configurations depending upon specific applications. Common implantable medical devices include stents, vena cava filters, grafts and aneurysm coils.

The endovascular system of a human body includes blood vessels, cerebral circulation system, tracheo-bronchial system, the biliary hepatic system, the esophageal bowel system, and the urinary tract system. Although exemplary stents implantable in blood vessels are described, they are applicable to the remaining endovascular system. Embodiments of the invention, some of which are described herein are readily adaptable for use in the repair of a variety of vessels, including but not limited to, treatment or repair in cases of aneurysm, ischemic stroke, carotid artery stenosis, saphenous vein graft, small vessel stenosis, or renal artery repair.

Stents are expandable prostheses employed to maintain vascular and endoluminal ducts or tracts of the human body open and unoccluded. For example, stents are now frequently used to maintain the patency of a coronary artery after dilation by a balloon angioplasty procedure. A stent is a typically a tubular meshwork structure having an exterior surface defined by a plurality of interconnected struts and spaces between the struts. The tubular structure is generally expandable from a first position, wherein the stent is sized for intravascular insertion, to a second position, wherein at least a portion of the exterior surface of the stent contacts and engages the vessel wall where the stent has been placed.

The expanding of the stent is accommodated by flexing and bending of the interconnected struts throughout the structure. The force for expansion can be applied externally as from a inflated balloon onto which the stent is loaded prior to placement, or the stent itself may be self-expanding. A myriad of strut patterns are known for achieving various design goals such as enhancing strength, maximizing the expansion ratio or coverage area, enhancing longitudinal flexibility or longitudinal stability upon expansion, etc. One pattern may be selected over another in an effort to optimize those parameters that are of particular importance for a particular application.

Figure 1A:
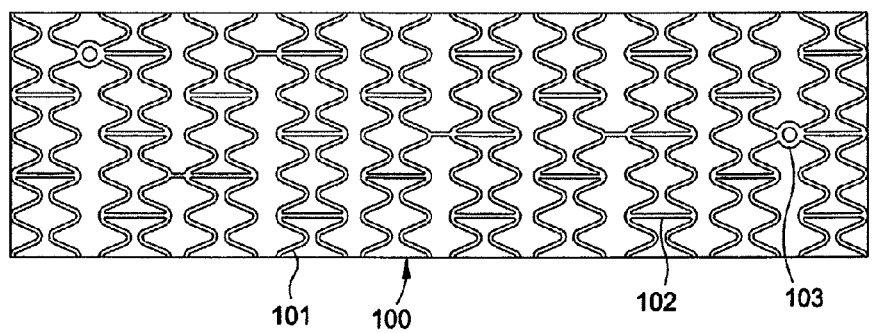
FIG. 1A illustrates an embodiment of a balloon expandable stent.
Figure 1B:
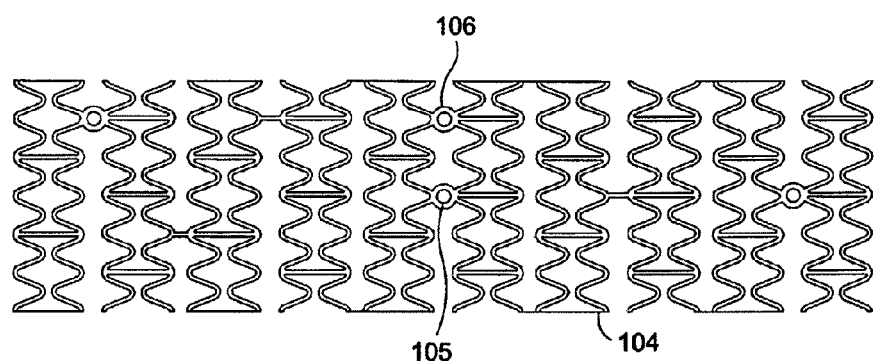
FIG. 1B illustrates another embodiment of a balloon expandable stent.

Illustrated in FIGS. 1A and 1B are two exemplary balloon expandable stent designs. FIG. 1A shows a tubular balloon expandable stent 100, further comprising end markers 103 to increase visibility of the stent 100 when viewed in situ using radiologic techniques. In some embodiments, the stent 100 is made of multiple circumstantial rings 101, where the ring connectors 102 connect two or three adjacent rings 101 and hold the rings in place. In FIG. 1A the end marker 103 is shown as a disc-shape. The shape of an end marker 103 is not critical to the function of the stent 100, and will be useful as long as the shape selected is effective to increase the radiographic visibility of the stent 100.

FIG. 1B illustrates a tubular balloon expandable stent 104, similar to the stent 100 shown in FIG. 1A, with the exception that the stent 104 comprises center markers 105, 106. The center markers 105, 106 help to aid in placing the stent over an aneurysm opening during an implantation operation. The center markers 105, 106 can be of the same material and shape as the end markers 103.

Figure 2:
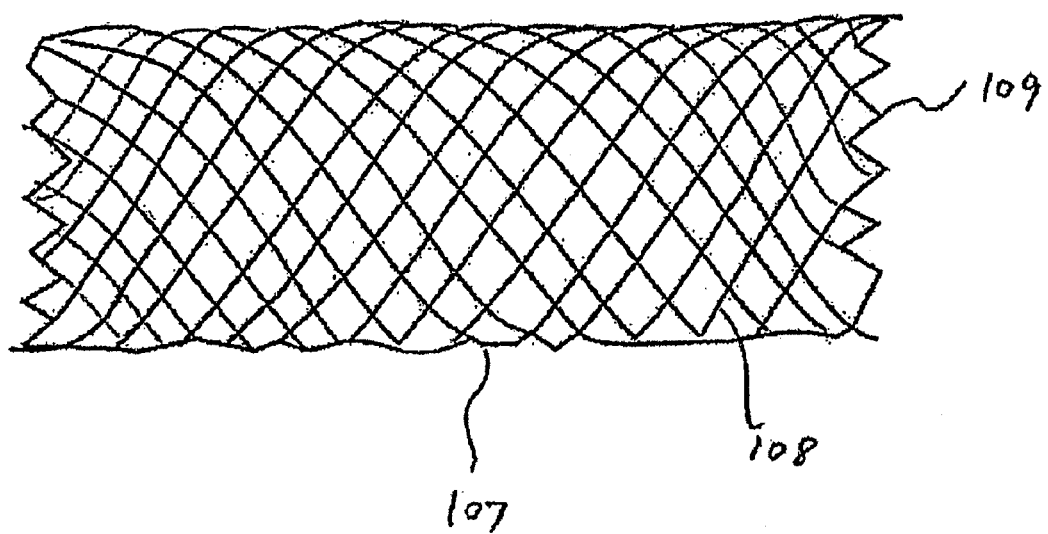
FIG. 2 illustrates a self-expanding stent.

FIG. 2 illustrates a self-expanding stent 107 made of wires or ribbons. While a self-expanding stent may have many designs, the stent 107 shown in FIG. 2 has a typical braided pattern 108 with welded ends 109. The stent 107 is designed to be relatively flexible along its longitudinal axis, to facilitate delivery through tortuous body lumens, but is still stiff and stable enough radially in the expanded state, such that it will serve to maintain the patency of a vessel lumen when implanted, for example in the lumen of an artery.

Figure 3:
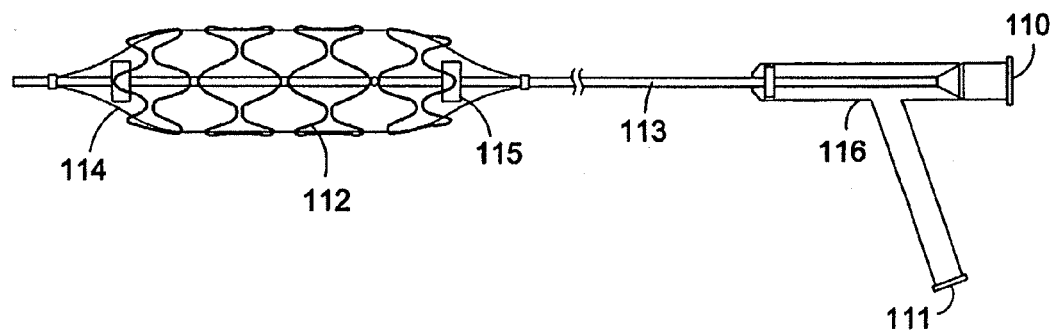
FIG. 3 illustrates a delivery system with a stent expanded on a balloon.

Illustrated in FIG. 3 is a delivery system and an expanded tubular stent 112, loaded over an expandable balloon 114. When the tubular stent 112 is fully expanded to its deployed diameter by inflation of the balloon 114, the latticework of struts takes on a shape in which adjacent crests undergo wide separation, and portions of the struts take on a transverse, almost fully lateral orientation relative to the longitudinal axis of the stent. Such lateral orientation of a plurality of the struts enables each fully opened cell to contribute to the firm mechanical support offered by the stent in its fully deployed condition, and insures a rigid structure that is highly resistant to recoil of the vessel wall following stent deployment.

While a stent 112 may be deployed by radial expansion under outwardly directed radial pressure exerted, for example, by active inflation of a balloon 114 of a balloon catheter on which the stent is mounted, the stent 112 may be self-expandable. In some instances, passive spring characteristics of a preformed elastic (i.e., self-opening) stent serve the purpose, while in others shape memory materials are used, such that upon activation by the appropriate energy source, the stent deforms into a pre-determined memorized shape. Regardless of design, in all cases the stent is expanded to engage the inner lining or inwardly facing surface of the vessel wall with sufficient resilience to allow some contraction, but also with sufficient stiffness to largely resist the natural recoil of the vessel wall following deployment.

Referring to the delivery system depicted in FIG. 3, there is included a guide wire lumen 110, a balloon inflating lumen 111, a connector 116, a balloon catheter shaft 113, and platinum marker bands 115 on the catheter shaft 113. The guide wire lumen 110 is used for introducing a guide wire in a balloon catheter, and the balloon inflating lumen 111 for inflating the balloon after the stent has been placed at a desired location. The connector 116 is used for separating the guide wire lumen 110 and the balloon inflating lumen 111. The balloon catheter shaft 113 carries the guide wire lumen 110 and the balloon inflating lumen 111 separately, with a typical length of about 135-170 cm. The ring markers 115 on the catheter shaft 113 are used so that the start of balloon tapers and the edges of the stent can be visualized by X-ray.

In FIG. 3, an expanded stent 112 is shown mounted onto an expanded balloon. Conveniently, the delivery catheter can be a conventional balloon dilation catheter used for angioplasty procedures. The balloon can be formed of suitable materials such as irradiated polyethylene, polyethylene terephthalate, polyvinylchloride, nylon, and copolymer nylons such as Pebax™. Other polymers may also be used. In order for the stent to remain in place on the balloon during delivery to the desired site within an artery, the stent is typically crimped onto the balloon. However, the precise design choices in delivery systems are not limiting to the scope of the disclosure.

In some embodiments, the delivery of the stent is accomplished as follows. The stent is first mounted onto an inflatable balloon on the distal extremity of the delivery catheter, and the stent is mechanically crimped onto the exterior of the folded balloon. The catheter/stent assembly is then introduced into the vasculature through a guiding catheter. A guide wire is disposed across the diseased arterial section and then the catheter/stent assembly is advanced over the guide wire that has been placed in the vessel until the stent is substantially located at the site of the diseased or damaged portion of the vessel. At this point, the balloon of the catheter is inflated, expanding the stent against the artery. The expanded stent engages the vessel wall, which serves to hold open the artery after the catheter is withdrawn.

Due to the formation of the stent from an elongated tube, the undulating component of the cylindrical elements of the stent is relatively flat in transverse cross-section, so that when the stent is expanded, the cylindrical elements are pressed into the wall of the vessel and as a result do not significantly interfere with the blood flow through the lumen. The cylindrical elements of the stent, which are pressed into the wall of the vessel, will eventually be overgrown with a layer of endothelial cells, further minimizing interference with blood flow that could be caused by the presence of the stent in the lumen. The closely spaced cylindrical elements, located at substantially regular intervals, provide uniform support for the wall of the artery, and consequently are well adopted to tack up and hold in place small flaps or dissections that may exists in the vessel wall.

Resilient or self-expanding prostheses can be deployed without dilation balloons. Self-expanding stents can be preselected according to the diameter of the blood vessel or other intended fixation site. While their deployment requires skill in stent positioning, such deployment does not require the additional skill of carefully dilating the balloon to plastically expand the prosthesis to the appropriate diameter, as the final diameter will be primarily a function of the stent design itself. Further, the size of the self-expanding stent is chosen such that when in place it remains at least slightly elastically compressed, and thus has a restoring force which facilitates acute fixation. By contrast, a plastically expanded stent must rely on the restoring force of deformed tissue, or on hooks, barbs, or other independent fixation elements included as part of the stent structure.

Self-expanding stents can be fashioned from resilient materials such as stainless steel, and the like, wherein the stent is loaded onto the delivery device in a compressed state, and upon placement at the desired location is allow to naturally elastically expand. Expandable stents can also be fashioned from shape memory materials such as nickel-titanium alloys and the like, wherein the stent is expanded from a first shape to a second shape by activation with an energy source such as heat, magnetic fields or an RF pulse for example.

The presence of a foreign object in a vessel, like a stent, can promote thrombus formation as blood flows through the vessel, and platelets contact the stent surface. This is a well-recognized problem in other areas of cardiovascular treatment, such as when artificial heart valves are implanted. In serious instances, clot formation can lead to acute blockage of the vessel. In addition, as the outward facing surface of the stent in contact or engagement with the inner lining of the vessel, tissue irritation can lead to an inflammatory reaction, further exacerbating restenosis due to localized hyperplasia. Stent design and use must take into account all these myriad factors.

Figure 4A:
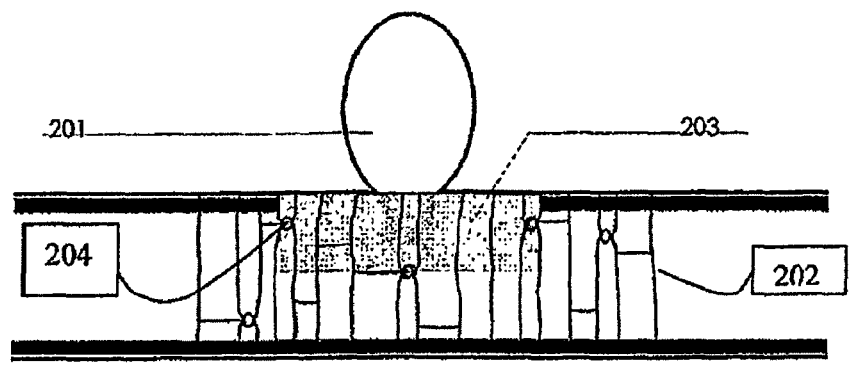
FIG. 4A is a view of a stent disposed in the location of an aneurysm
Figure 4B:
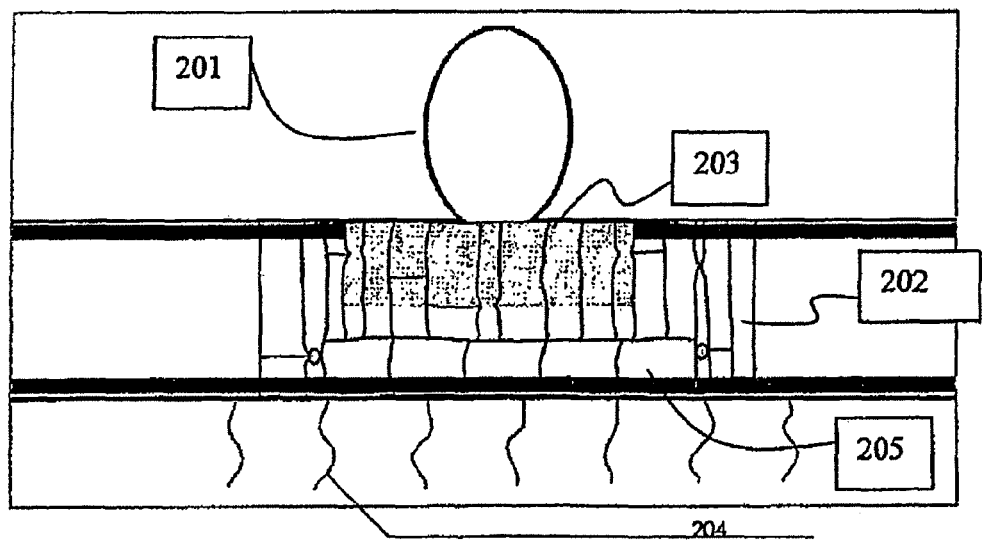
FIG. 4B is a second diagrammatic view of a stent disposed in the location of an aneurysm.

In one embodiment, illustrated in FIGS. 4A, and 4B, there is provided an intracranial stent 202 and for use in the repair of stenotic lesions and aneurysms 201. Due to the characteristics of intracranial blood vessels, the intracranial stents 202 are designed to be very flexible, low profile (diameter of 0.8 mm or less when crimped onto the delivery catheter) and having a thin wall (less than 0.1 mm). As they are used in small vessels, intracranial stents 202 do not necessarily possess, or need, the highest possible radial strength.

As shown in FIG. 4A, the intracranial stent 202 is located at the site of an aneurysm 201. A membrane 203 partially covers the stent 202 and is positioned to seal the neck, thus blocking blood flow to the aneurysm 201. Blocking blood flow is an important function of the stent, as it reduces the risk of aneurysm rupture, which can cause neurological deficit or even death if it occurs intracranially, and promotes the formation of a thrombus and resolution of the aneurysm. Radiopaque markers 204 can be located in the middle of the stent 202 to provide visibility of the stent 202 during operation and post-operation inspection.

In FIG. 4B, a portion of the stent 202 is shown to include open "cells" 205. This design avoids blocking perforator vessels (sometimes called perforators), small capillary vessels that have important and distinctive blood supply functions. It is possible that tubular stents can block perforators and inhibit important functions of these vessels, which may be related, but not limited the general health of the vessel and surrounding tissue. Moreover, stents covered with non-porous membranes suffer from the disadvantage that the membrane portion of the stent can block the perforators.

Figure 5:
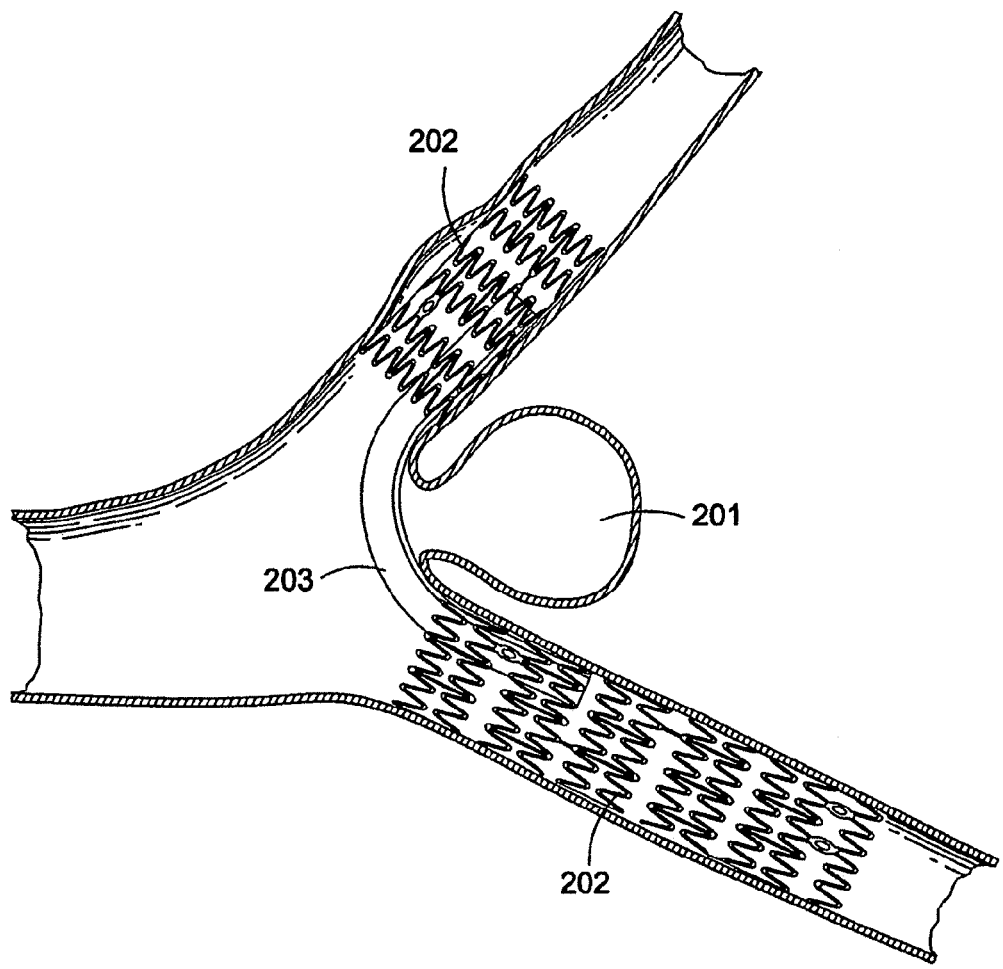
FIG. 5 illustrates a membrane joining two stents for treating a bifurcation aneurysm.

Stents may also be used to treat a number of different types of aneurysms, including bifurcation aneurysm, as shown in FIG. 5. For example, as illustrated, an intracranial aneurysm 201 can be treated with a stent 202 and membrane 203 to effectively prevent ischemic and hemorrhagic stroke. At least 30 to 35% of aneurysms are located at bifurcation sites of intracranial vessels. In this embodiment, the membrane 203 is one-sided and non-circumferential. In some embodiments the membrane may be circumferential and may cover substantially the entire stent. The stents 202 are joined by the membrane 203, which covers the aneurysm neck 201. The same pattern can be applicable to self-expandable (super-elastic) or balloon expandable (stainless steel, CoCr, PtIr alloys) stents. Thus, the intracranial stent 202 coupled with a membrane 203 acts as a scaffold to open clogged arteries, and the membrane provides a cover to prevent blood flow to the aneurysm 201. Obstructing blood supply to the aneurysm 201 isolates the aneurysm 201 from normal blood circulation, eventually resulting in thrombus formation within the aneurysm. Complete obstruction of the aneurysm 201 may not be necessary in order to achieve initiation of an aneurytic thrombus.

Table 1 provides a table with exemplary dimensions for an intracranial stent 202 designed for use with a membrane 203. The membrane 203 is biocompatible, has good adhesion to stent struts made from a variety of materials including, but not limited to stainless steel, titanium and nickel alloys and the like. The membrane forms an ultra-thin film that is porous as opposed to being a solid film, having holes or pores included during the process of manufacturing the membrane. In some embodiments, the pore size and material coverage area are selected to prevent blockage of perforator vessels, and while restricting blood flow to the aneurysm.

TABLE 1

Typical Dimensions of Manufactured Stents for Intracranial Use

| Dimensions | As Manufactured | Crimped | Expanded |
| --- | --- | --- | --- |
| Strut Thickness |  | 0.003" (0.076 mm) |  |
| Outer Diameter | 0.080" (2.03 mm) | 0.040" (1.02 mm) | 0.16"-0.20" (4.0-5.0 mm) |
| Distance Between Struts | 0.031" (0.80 mm) | 0.016" (0.40 mm) | 0.079" (2.0 mm) |

In some embodiments, the membrane 203 is made from a thin film generally in a range of from about 25 µm to about 125 µm in thickness, measured in the as-manufactured state, and is from about 5 µm to about 25 µm thick, as measured in the deployed state (expanded state). The film has good expandability, and can be expanded up to about 400% using relatively low force. The membrane 203 also has good chemical stability at ambient conditions allowing for extended storage prior to use, and is stable under sterilization conditions (ethanol). Examples of physical properties of the membrane are a hardness of about 75 A (measured with a Shore durometer), tensile strength up to about 7500 p.s.i., and elongation of up to about 500%.

Figure 6:
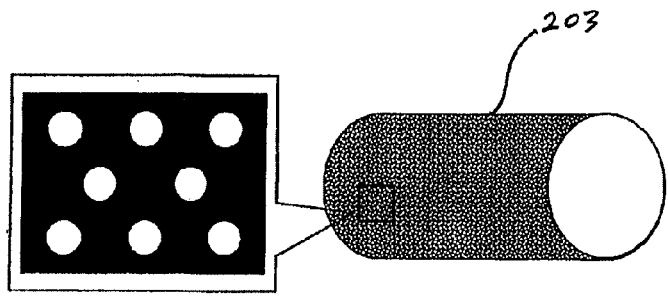
FIG. 6 illustrates a stent with a membrane having a pattern of pores.
Figure 7:
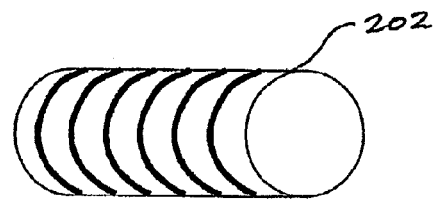
FIG. 7 illustrates a stent having polymer strips.
Figure 8:
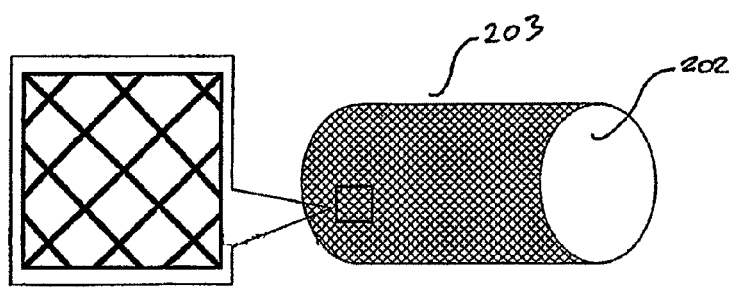
FIG. 8 illustrates a stent with a membrane having a mesh.

Conveniently, membranes can be made porous, and if desired uniformly porous, by drilling holes into a solid film. In this way a stent 202 covered by a uniformly porous membrane 203 can be provided as illustrated in FIG. 6. The exploded view of FIG. 6 depicts an area of a membrane having uniformly spaced pores. The pore diameter is generally in the range of about 1-150 µm, while the distance between pores is generally less than about 100 µm. Porosity of a stent 202 covered by a membrane can be varied in other ways, including covering the stent 202 with membrane strips as shown in FIG. 7, or by providing a stent 202 covered with a mesh like membrane 203, as in FIG. 8. Porosity can also be varied by changing pore diameter, or the number of pores per unit area of the membrane.

Where the stent is covered with membrane strips, as shown in FIG. 7, the strips of membrane 203 can be wrapped laterally around the stent 202. Securing the strips to the stent 202 may be accomplished by interlacing the strips above and below the struts of the stent (not shown). Typically the width of strips would be less than 0.075 mm, and the distance between adjacent strips would be less than about 100 µm.

Where a mesh or woven membrane is used, a sheet of woven membrane 203 can be wrapped circumferentially around the stent 202, as illustrated in FIG. 8. In one embodiment the mesh size is about 0.025 to 0.05 mm, while the width of the polymer is typically less than about 100 µm.

Figure 9:
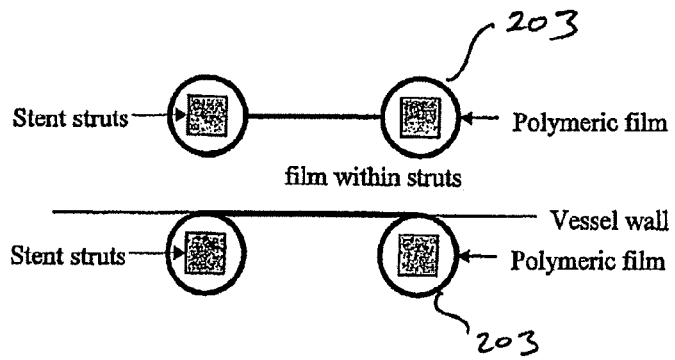
FIG. 9 illustrates a membrane secured to the struts of a stent.
Figure 10:
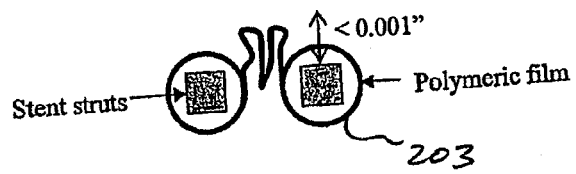
FIG. 10 illustrates a membrane before the stent is deployed.
Figure 11:
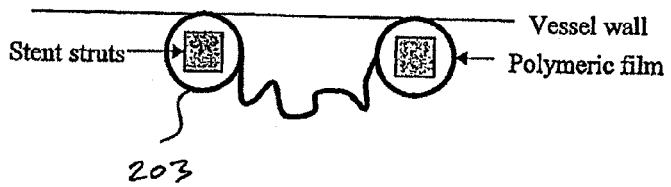
FIG. 11 illustrates a membrane flipping in side the vessel rather than staying close to the vessel wall.

In some embodiments, the membrane 203 completely surrounds the stent struts, and forms a stable film between the struts, as shown in FIGS. 9A and B. The film between struts can be disposed centrally between struts as in FIG. 9A, or outside struts as shown in FIG. 9B. FIG. 10 illustrates a membrane and stent in the unexpanded state, prior to deployment. Where the film is located outside the struts, as in FIG. 9B, there is a further advantage provided in that the membrane will tend to maintain closer contact with the vessel wall, and will avoid "flipping" toward the inside the vessel, as is depicted in FIG. 11.

Figure 12:
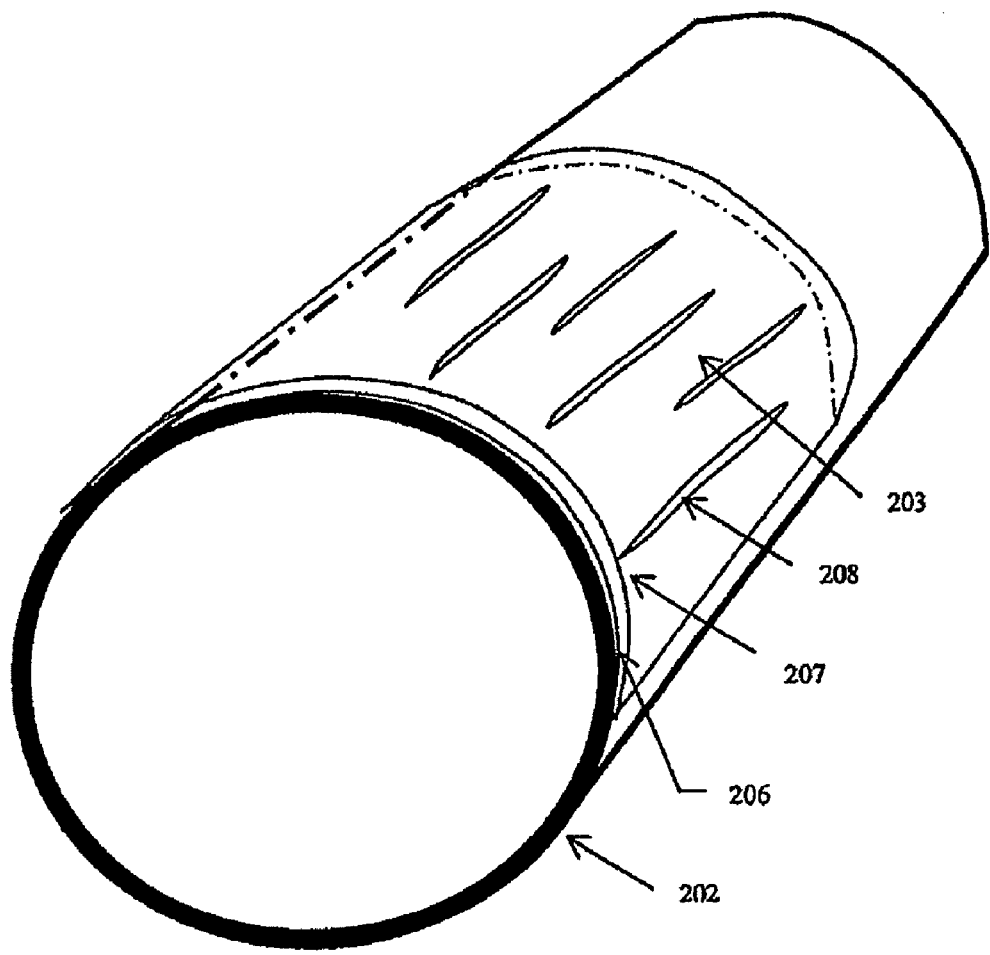
FIG. 12 illustrates a stent partially covered by a membrane having pockets for release of therapeutically effective agents.

Implantable medical devices can also be used to deliver drugs or reagents to specific locations within the vascular system of a human body. As shown in FIG. 12, a membrane 203 can comprise pockets 208 which serve as reservoirs for drugs or reagents intended for delivery into the region of a vessel wall or lumen. In certain embodiments, the membrane 203 comprises a first layer 206 attached to the outer surface of an implantable medical device such as a stent 202. An intermediate layer is attached to the first layer wherein the intermediate layer comprises at least two circumferential strips being separated from each other and a second layer covering the first layer and the intermediate layer.

The spaces surrounded by the first layer, and the circumferential strips and the second layer form the pockets 208 that serve as receptacles for drugs or reagents. In other embodiments, the intermediate layer includes at least one opening so that the pockets can be formed within the openings. The shapes and sizes of the openings can be varied in accordance with specific applications. The stent 202 can be partially covered by a membrane 203 that comprises a first layer 206 and a second layer 207.

Figure 13:
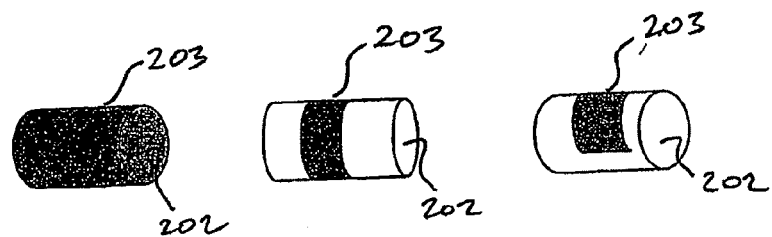
FIG. 13 illustrates a stent with a membrane secured at three different positions and with three different sizes.

In some embodiments, the membrane 203 can cover the entire stent, or portions of the stent 202, as is shown in FIG. 13. Thus, the size of the membrane can be varied if desired to particularly suit the location where the stent is to be placed.

Many polymeric materials are suitable for making the layers of the membrane 203. Typically, one first layer is disposed onto the outer surface of a stent. The first layer has a thickness of about 50-125 µm, with pore sizes of about 20-30 µm as a nominal initial diameter. In certain embodiments, the first layer can serve as an independent membrane 203 to mechanically cover and seal the aneurysm 201. The first and/or second layers can be comprised of biodegradable material, and function as a drug or reagent carrier in order to provide sustained release functionality.

It is desirable that the intermediate layer be formed of a material which can fuse to the first and second layers or attached to the first layer in a different manner. In certain embodiments, the intermediate layer may be merged with the first layer to form a single layer with recessions within the outer surface of the merged layer. The second and intermediate layers can be made of biodegradable material that include drugs or other reagents for immediate or sustained release. After the biodegradable material is dissipated through the degradation process, the membrane 203 is still intact, providing vessel support. The second layer can also be composed of a polymeric material. In some embodiments, the second layer has a thickness of about 25-50 μm, with pore sizes ranging from about 70-100 μm.

The polymeric layers may be fashioned from a material selected from the group consisting of fluoropolymers, polyimides, silicones, polyurethanes, polyurethanes ethers, polyurethane esters, polyurethaneureas and mixtures and copolymers thereof. Biodegradable polymers can include polylactide, poly(lactide-co-glycolide), poly-orthoesters, polyphosphazenes, polyanhydrides, or polyphosphoesters. The fusible polymeric layers may be bonded by adhering, laminating, or suturing. The fusion of the polymeric layers may be achieved by various techniques such as heat-sealing, solvent bonding, adhesive bonding or the use of coatings.

Types of drugs or reagents that may prove beneficial include substances that reduce the thrombogenic, inflammatory or smooth muscle cell proliferation response due to the implanted device. For example, cell proliferation inhibitors can be delivered in order to reduce or inhibit smooth muscle cell proliferation. In intracranial or some other applications fibrin sealants can be used and delivered to seal aneurysm neck and provide fibroblasts and endothelial cells growth. Specific examples of drugs or reagents include heparin, phosporylcholine, albumin, dexamethasone, paclitaxel and vascular endothelial growth factor (VEGF). This list is not exhaustive, and other factors known to regulate inflammatory responses, cellular proliferation, thrombogenesis and other processes related to reaction to foreign bodies are contemplated to be useful within the scope of the disclosure.

The drug or reagents can be incorporated into the implantable medical devices in various ways. For example the drug or reagent can be injected in the form of a gel, liquid or powder into the pockets. Alternatively the drug or reagent can be supplied in a powder which has been formed into a solid tablet composition, positioned in receptacles placed in the device.

It is at times desirable to provide a stent that is highly flexible and of small profile in order to effect treat vessels of very small caliber, for example, intracranial vessels with lumen diameters ranging in size from about 1.5 mm to about 5.0 mm. High flexibility allows the stent to be advanced along the anatomy of the intracranial circulation.

Figure 14:
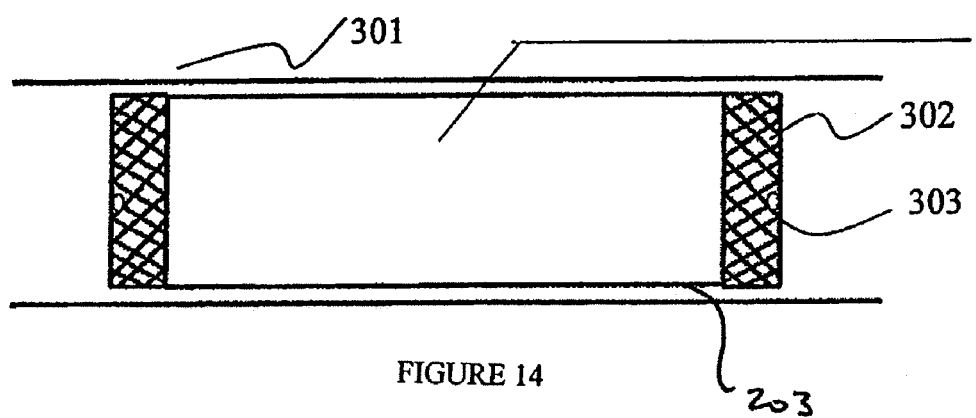
FIG. 14 illustrates a sleeve as a membrane supported by two ring-like stents.

In some embodiments, as illustrated in FIG. 14, a membrane 203 is embodied as a sleeve 301 supported by two ring-like short stents 302 at both ends of a device so that the membrane 203 covers the whole area of the device 302. There is no scaffold support in the middle of the device 302. Radiopaque markers 303 are located at both ends of the stent 302. Depending on the particular application, the rings can be balloon expandable and made from stainless steel or self-expandable and made from NiTi (memory shaped nickel-titanium alloy), and the like.

The membrane 203 is part of the stent structure and is effective to occlude the aneurysm neck and "recanalize" a diseased, damaged, or weakened vessel, leading to healing of the vessel and elimination of the aneurysm. The use of a stent as shown in FIG. 14, further obviates the need for coiling procedures, which are at times used in conjunction with stents to treat wide neck aneurysms. The present apparatus and methods are also a preferred treatment solution for cc fistula ruptured in cavernous sinus, pseudoaneurysms, saccular aneurysms.

In some embodiments, there is provided a porous membrane as part of the device. The membrane 203 has a system of holes or pores 25 with pore diameter 21 on the order of about 1 to 100 μm, and borders 23 between the pores have a width generally less than about 100 μm, as shown in FIG. 15. To provide a membrane of variable porosity, pore spacing and even pore size can be varied in different areas of the membrane.

It has been further discovered that a membrane having uniform porosity can be effective in blocking blood flow to an aneurysm while maintaining flow to perforator vessels.

In some embodiments, pore spacing (the distance between adjacent pores) can be in a range of from about 40 to 100 μm. To produce a membrane of uniform porosity, pore diameter 21, and interpore spacing 22, will be generally equidistant, as in FIG. 16, over substantially the entire area of the membrane. Depending on the size and number of pores in the membrane, the membrane can be described as being macroporous or microporous. For example, in a macroporous membrane, an schematic of which is shown in FIG. 17, pores 25, may range in size from about 10 to 100 μm, and are relatively equally spaced within the membrane material 20. Alternatively, in a microporous membrane, pore diameter may be on the order of about 1 to 10 μm, and again are generally equally spaced in a uniformly porous section of a membrane. The pore sizes shown in FIGS. 17 and 18 are only examples, and a range of pore sizes are expected to be useful in an implantable device.

Furthermore, the characterization of a membrane as either macro- or microporous is not limiting to the disclosure. The functionality of the membrane is dependent on pore diameter and pore spacing, which are described in terms of physical measurement units, and how the particular physical dimensions of the membrane pores operate in situ to regulate blood flow. In either case, membranes having porous sections of uniform porosity can be fashioned by selecting a desired pore diameter and pore spacing combination. As is seen in the data presented below, various combinations of pore diameter and pore spacing are effective to provide a membrane of optimal porosity over a range of deployed sizes. Thus, a porous membrane 203 is able to significantly improve hemodynamics around the aneurysm 201, since it has a lower delivery profile and is more flexible, as compared to a stent 202 with a solid membrane.

One application for a device having a macroporous membrane is to treat aneurysms within close proximity of branches or perforators. Another specific application is the treatment of an intracranial saccular or wide neck aneurysm located above the ophthalmic artery where perforators extend from the parent artery within close proximity of the aneurysm. Microporous devices are suitable for use in areas where perfusion of perforators is of less immediate concern. Thus, the micro-porous device is used for conditions which require total coverage to immediately block blood flow, for example, a caroticocavernous fistula, or where there is little or no risk of blocking perforators, for example, below the ophthalmic artery.

The device may be used for the treatment of endovascular disease such as aneurysms, arteriovenous malformations (AVM's) and caroticocavernous fistulas. The device may also be useful in other vessel related applications such as treatment or repair in cases of ischemic stroke, carotid artery stenosis, saphenous vein graft, small vessel stenosis, or renal artery repair. The pore patterns are designed with consideration of factors such as specific flow conditions of blood vessels, and the location of the vessel being repaired.

Figure 19A:
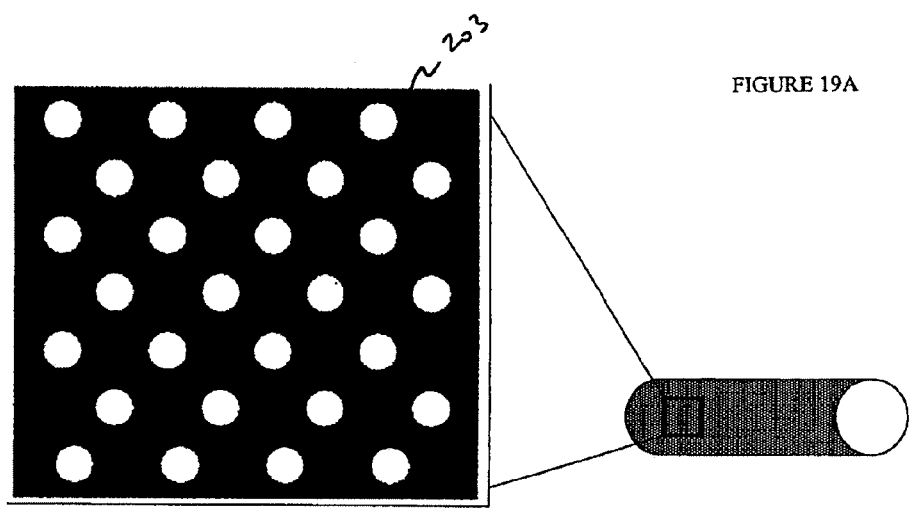
FIG. 19A is a graphical representation of a membrane as manufactured, (i.e. unexpanded) state.
Figure 19B:
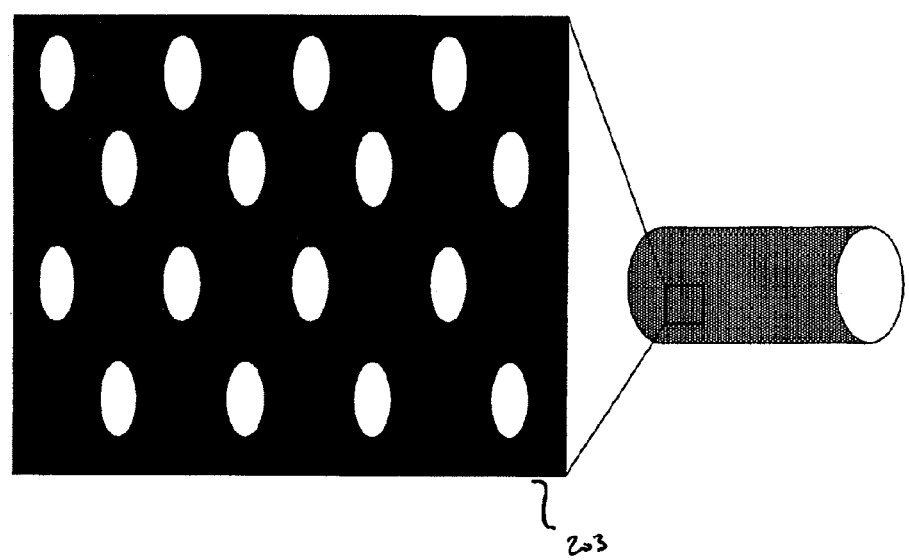
FIG. 19B illustrates a membrane in the expanded (i.e. deployed) state.

The design of the porous section of a membrane is therefore initially determined according to the intended application of the device, and three main factors, pore size 21, bridge dimensions 22, 23, and material ratio of the membrane. Pore size 21 can be measured in the "as designed and manufactured" (i.e. unexpanded) and "as deployed" (i.e. expanded) states. Typically, pore size in the unexpanded state is about 1.5 to 2.5 times smaller than pore size after the membrane has been expanded to its deployed size. This is depicted in FIGS. 19A and B.

Bridge dimensions 22, 23 refer to the shortest distance separating one pore 25 from its adjacent pores, as shown in FIG. 15. Each pore 25 may be spaced from adjacent pores at variable distances, or as shown in one embodiment depicted in FIG. 16, at generally equal distance. In a uniformly porous section of a membrane the pore spacing will be relatively equidistant throughout the membrane. Similar to pore size 21, bridge dimensions 22, 23 can also be measured in two states, as designed and manufactured, or as deployed. The as designed and manufactured bridge dimensions are typically larger than the as deployed bridge dimension 22, 23 by a factor of 1 to 2, since stretching of the membrane during deployment reduces the size of the bridge.

Membrane Porosity

The relative porosity of a porous section of a membrane will be dictated by the size of individual pores and the number of pores per unit area (i.e. pore density). As used herein, the term "porous section" refers to that area of a membrane that includes substantially all the pores of the membrane. Coverage and porosity can both be described in terms of a relationship between the area of the apparent area of the porous section of the membrane corresponding to membrane material, versus that corresponding to the pores. Thus, the material ratio is the fraction of a membrane area that corresponds to membrane material, or in other terms, total apparent area or the porous section(100%)−pore area(%)=material ratio(%). As used herein, the term "material ratio" refers in particular to the membrane material versus pore area in a porous section of a membrane.

As indicated, material ratio is conveniently expressed as a percentage. So, for example, a membrane lacking pores has a material ratio=100%, while in a membrane with 20% of its total area encompassed by pores, the material ratio=80%. Likewise, porosity can also be expressed as a percentage, where porosity(%)=total area of the porous section of the membrane(100%)−material ratio(%). A membrane having a material ratio of 75% would have a porosity of 25%. Both material ratio and porosity can be described in membranes in the "as manufactured" and "as deployed" stages. In some embodiments, the overall material ratio in the deployed state can range between about 25% to about 80%.

It has been discovered that a membrane of uniform porosity can be effective to promote healing of an aneurysm if the material ratio of the porous section of the membrane is within a certain range when the membrane is in the deployed state. Thus, in some embodiments the material ratio of the porous section of the membrane is preferably in a range between about 70% to 80%, with the optimal material ratio considered to be about 75%, when the membrane is deployed. Uniformity is achieved by maintaining the variance in the size of pores, as well as the spacing between pores in a porous section of the membrane, while an optimal material ratio is achieved on the basis of particular pore diameters and spacing.

The porous section can also be conceptually divided into a number (n) of porous regions, wherein the area of each of the n regions is substantially 1/n of the total area of the porous section of the membrane. For example, in some embodiments, there can be 2, 3, 4, 5 or more porous regions, where each of the regions has substantially the same porosity as each of the other porous regions existing with the porous section of the membrane. The porosity of either a region or the porous section as a whole is determined by the combination of pore size and pore spacing.

While the interpore size variance will be substantially uniform over the area of a porous section within each individual membrane, it is to be recognized that it is possible to provide different membranes with different numbers of pores, or different pore spacing as a way in which to provide a set of membranes of varying porosity. In this way it is possible to have a set of membranes with a range of porosities, any one of which can be chosen based on the requirement in a particular application. Thus depending on a variety of factors, a membrane could be produced with properties that would make it particularly well-suited for use in aiding in the stabilization and repair of a particular vessel, while for another application a membrane of a different porosity might be preferable, and could be fashioned accordingly.

Porosity of the membrane is considered optimal when the membrane permits blood supply to perforators of main arteries while reducing blood circulation to the diseased, damaged or weakened portion of the vessel wall being repaired. In addition, a further benefit may be realized by selecting a membrane having a porosity that enables enhanced endothelial cell migration and tissue ingrowth for faster endothelialization. The membrane as disclosed may be used in devices designed for a variety of vessel repair applications other than aneurysms. These may include, but are not limited to, use in the treatment of ischemic stroke, carotid artery stenosis, saphenous vein graft, small vessel stenosis, or renal artery repair.

As indicated above, part of the novelty described in the present disclosure lies in the discovery that a stent having a uniformly porous membrane is capable of supporting a vessel wall at the site of an aneurysm, maintaining the patency of parent and perforator vessels, while restricting blood flow to the aneurysm itself. In prior art devices these functionalities were achieved using membranes with non-uniform porosity, or regions of varying porosity. By providing these features the device promotes more rapid and more effective healing of an aneurysm, while at the same time providing a device that is more universally adaptable for use in a wider variety of in vivo locations than previously possible, and simpler to manufacture and use.

Figure 20:
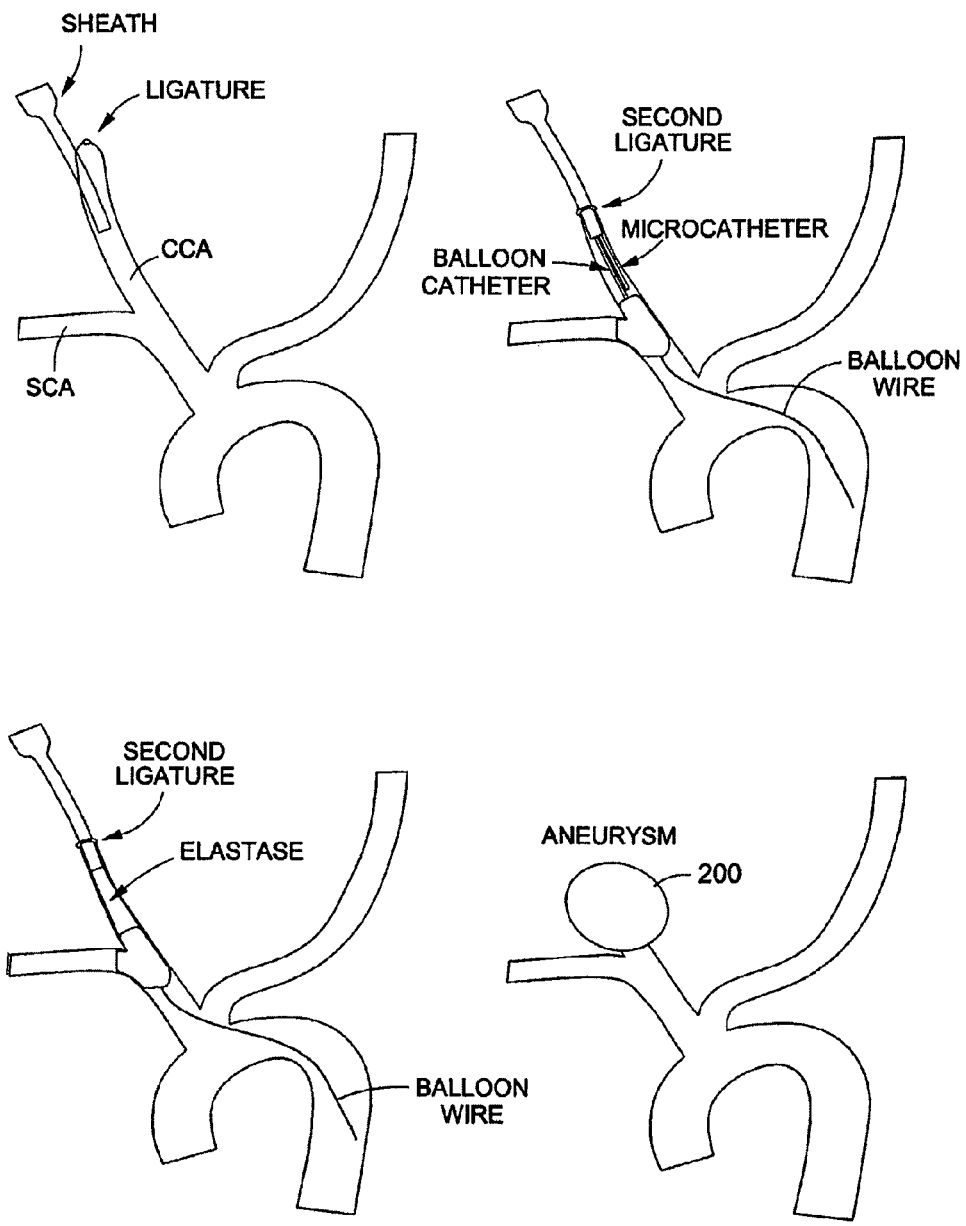
FIG. 20 illustrates an experimental model for inducing aneurysms using elastase delivered by a catheter.

This has been confirmed experimentally in an animal aneurysm model. In this model system, aneurysms are induced by infusion of elastase into the lumen of a vessel by way of a catheter, as diagrammed in FIG. 20 (See: Miskolczi, L. et al., Rapid saccular aneurysm induction by elastase application in vitro, Neurosurgery (1997) 41: 220-229; Miskolczi, L. et al., Saccular aneurysm induction by elastase digestion of the arterial wall, Neurosurgery (1997) 43: 595-600). An example aneurysm 200 produced by this method is shown in FIG. 21A.

Figure 21A:
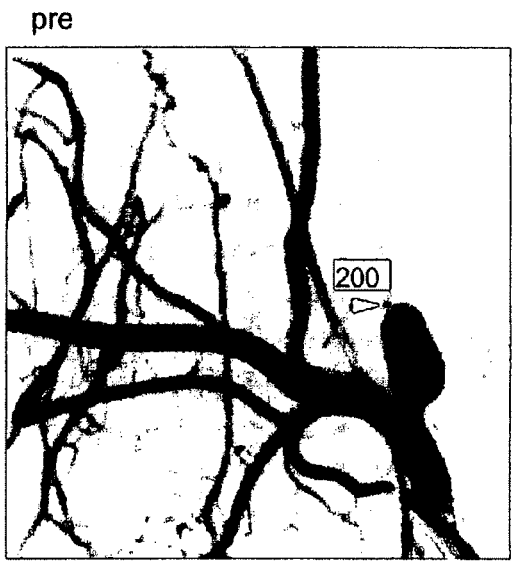
FIG. 21A illustrates a radiographic view of an aneurysm prior to treatment of an experimentally induced aneurysm.
Figure 21B:
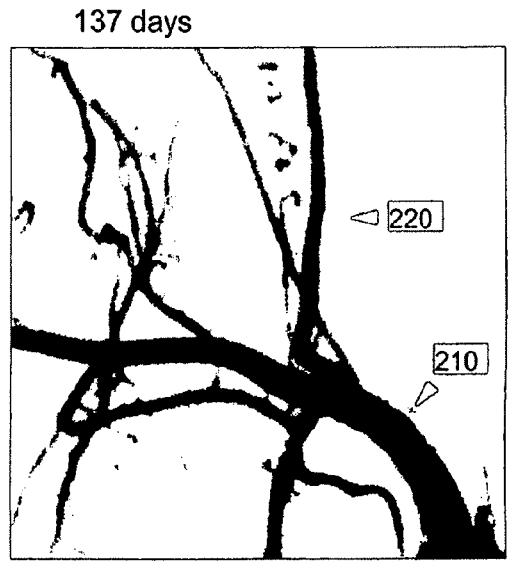
FIG. 21B illustrates a radiographic view of the same aneurysm, 137 days after the start of treatment with an embodiment of a membrane-covered stent.
Figure 21C:
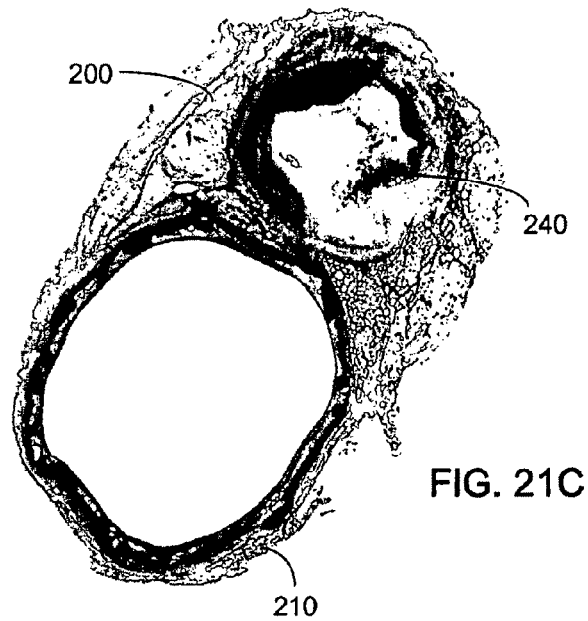
FIG. 21C is a histological section taken at the level of a thrombosed aneurysm.

In the illustrated experiment, a stent was deployed at the site of the aneurysm shown in FIG. 21A, in order to support the vessel wall and to aid in repair of the damaged area. As can be seen in FIG. 20B, after 137 days blood flow to the aneurysm had ceased, while the patency and flow in the parent vessel 210 and a nearby perforator vessel 220 was maintained. A histological section through the vessel at the site of the aneurysm, shown in FIG. 21C, reveals that a thrombus 240 formed at the site of the aneurysm, indicating that the aneurysm had become substantially occluded. Note that the parent vessel 210 is open and unobstructed. This process of remodeling of the aneurysm is diagrammed in FIG. 22.

Results from a series of studies like these have suggested that the material ratio of the membrane for optimal efficacy should be about 75%, or at least in the range of about 70-80%. In order to achieve this optimal porosity, several factors are considered. For example, the size as manufactured relative to the deployed size will be important, as the change in pore area occurs at a different rate than does the overall area of the membrane.

The material ratio has therefore been determined for membranes of varying pore diameter, pore spacing, and degree of expansion from the manufactured size to various deployment sizes, in order to evaluate what pore spacing and pore size can provide a material ratio in the range of about 70-80%, at deployed sizes ranging from 2.5-5.0 mm. In the examples described, material ratio in the unexpanded state ranged from 86-96% depending on the pore size and spacing. To determine the material ratio in the expanded state, membranes were expanded as they would be during deployment, and the pore diameter measured at selected areas. The material ratio was then determined as follows:

$A$=total area of porous section of membrane, $P$=total area of pores;

Porosity=$(P \div A) \times 100\%$; Material Ratio=$(1-(P \div A)) \times 100\%$ In the data shown in Table 2, two membranes having porous sections with different pore size and pore spacing were evaluated. Porous 30/70 (30/70 membrane) refers to a membrane manufactured with 30 μm pores with an interpore spacing of 70 μm in the unexpanded state; likewise, Macroporous 40/60 (40/60 membrane) refers to a membrane with 40 μm pores and an interpore spacing of 60 μm, again, in the unexpanded state.

TABLE 2

Effect of Deployment Size on Material Ratio

| Configuration | Diameter of Stent | | | | |
|---|---|---|---|---|---|
| | 2.0 mm (as made) | 2.5 mm | 3.0 mm | 3.5 mm | 4.0 mm |
| Macroporous 30/70 Pore Diameter: 30 μm Pore Spacing: 70 μm | 92% | 87% | 80% | 75% | 69% |
| Macroporous 40/60 Pore Diameter: 40 μm Pore Spacing: 60 μm | 86% | 78% | 72% | 64% | 56% |

As the data in Table 2 shows, when a membrane is expanded from its manufactured size (here 2.0 mm) to various deployed sizes, ranging from 2.5 to 4.0 mm, the material ratio decreases. Thus, depending on the initial pore size and density, the optimal material ratio of about 70-80% will be achieved at different degrees of expansion, analogous to the various deployment diameters of the stent being covered by the membrane.

For example, in a 30/70 membrane, material ratios within the optimal desired range of about 70-80% are substantially achieved at deployment diameters of about 3.0 to about 4.0 mm, when starting with a manufactured size of 2.0 mm. For a 40/60 membrane the optimal material ratio is achieved at a point between 2.0 to 2.5 mm, up to about 3.0 to 3.5 mm.

By extending this analysis it is possible to determine the number of different stent pore patterns, the pattern being the combination of pore size and interpore spacing, necessary to provide about a 70-80% material ratio over wide range of stent diameters. The goal is to know beforehand, the combination of pore size and spacing that, when the membrane is expanded to its deployed size, will provide a material ratio within the desired range of about 70-80% and preferably about 75%.

For example, the calculations in Table 3 show that with three different membrane patterns, it is possible to achieve a material ratio in the range of about 70-80% using a stent with a manufactured size of 2.2 mm, expanded to deployment sizes ranging from 2.5-5.0 mm. In these cases, the material ratio of the membrane in the unexpanded state ranges from 86-96%.

TABLE 3

Relationship of Material Ratio and Stent Diameter

| Final diameter of patch | Stent size | Pore diameter, μm | Interpore distance, μm | % coverage as deployed | % coverage as manufactured at 2.2 mm |
|---|---|---|---|---|---|
| 2.5, 2.75, 3.0 mm | 2.5/3.0 mm | 40 | 60 | 70-80% | 86% |
| 3.25, 3.5, 3.75, 4.0 mm | 3.5/4.0 mm | 30 | 70 | 70-80% | 92% |
| 4.25, 4.5, 4.75, 5.0 mm | 4.5/5.0 mm | 20 | 75 | 70-80% | 96% |

Figure 23:
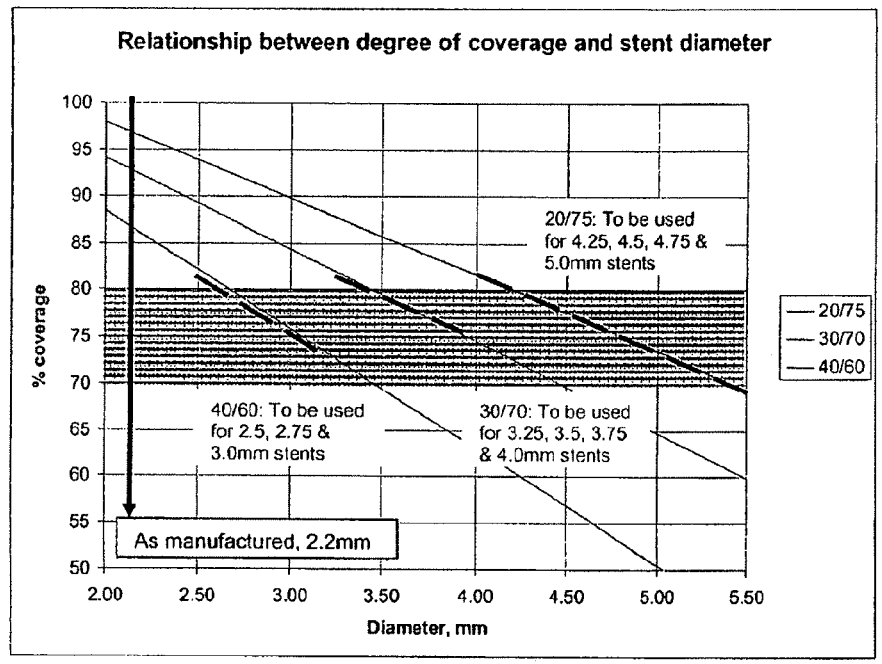
FIG. 23 is a graph of the relationship between coverage ratio and stent diameter.

These results are further exemplified in FIG. 23, which shows a graphic analysis of the relationship between pore diameter, pore spacing and deployment size for three different pore patterns, and the material ratio that results upon deployment to various diameters. In each case the material ratio of the membrane is plotted as a function of diameter of the stent in the expanded state. In all cases, the stents are manufactured at a size of about 2.2 mm. A surgeon, simply by knowing the size of the vessel to be repaired, can readily select a stent and membrane combination optimized to provide a 70-80% material ratio within a porous section of the membrane when the device is deployed, and achieve effective healing and repair of an aneurysm.

As shown in FIG. 23, for a 40/60 membrane, deployment sizes ranging from about 2.7 mm to about 3.5 mm will provide a coverage area in the desired range of about 70-80%. For a 30/70 membrane, deployment diameters ranging from about 3.5 mm to about 4.5 mm will result in a coverage area in the desired range of about 70-80%, and for a 20/75 membrane (i.e. 20 μm pore diameter; 75 μm pore spacing) deployment sizes ranging from about 4.2 mm to about 5.4 mm will provide a coverage area in the desired range of about 70-80%. Thus, a material ratio in the range of about 70-80% can be achieved over deployment sizes of 2.7-5.4 mm by selecting the membrane from a set of only three membranes. It is contemplated that by varying pore spacing and pore diameter, as well as with membranes made from various materials, greater flexibility in obtaining optimum material ratio at the widest variety of deployed sizes is possible.

Figure 24A:
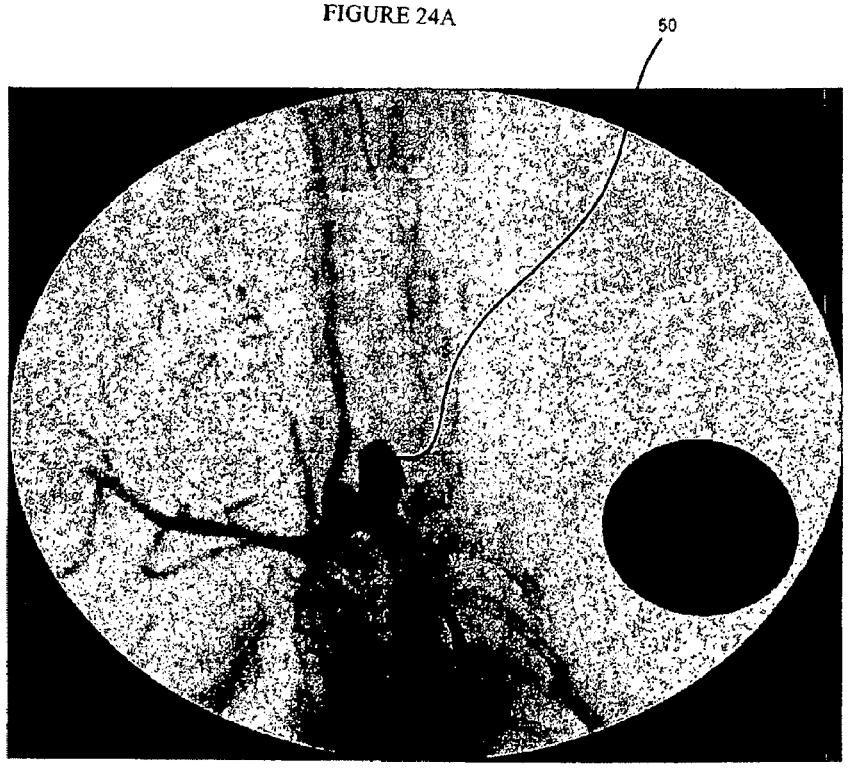
FIG. 24A is a radiographic view of an aneurysm located in the subclavian artery of a rabbit.
Figure 24B:
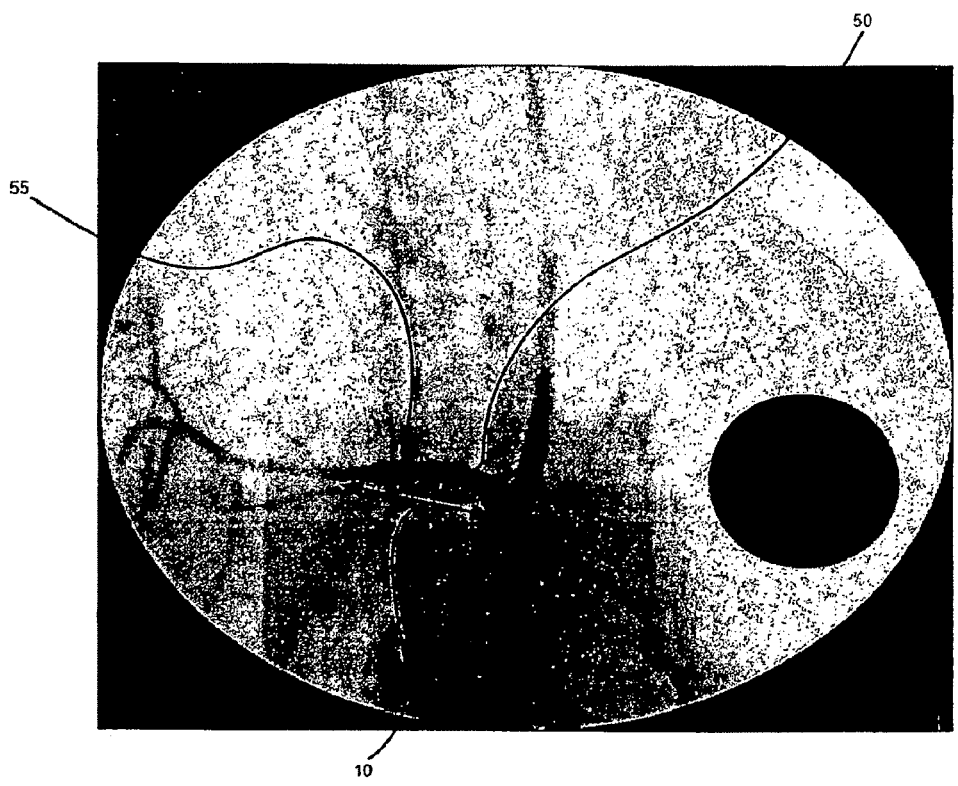
FIG. 24B is the artery shown in FIG. 25A subsequent to treatment.

In practice, and as shown in FIGS. 24A and B, an embodiment of a device 10 effectively reduces blood flow into an aneurysm 50. Reducing flow to the aneurysm induces intraaneurysmal thrombosis. FIG. 24A shows an aneurysm 50 located in the subclavian artery of a rabbit. In FIG. 24B, the results show that within a few hours deployment of the device 10 in the vessel 5, blood supply to the body of the aneurysm 50 is effectively stopped. Significantly, the pore pattern of the membrane continues to allow an uninterrupted supply of blood through perforator vessels 55 located proximal to the deployed device 10. The device 10 uses the antagonistic relationship between the sufficient reduction of blood supply to disrupt and thus heal an aneurysm 50 and the maintenance of sufficient blood supply vital to keep the perforators 55 patent.

For example, consider an aneurysm 50 with aneurysm neck diameter of about 6 mm and height of about 10 mm. If the aneurysm neck is covered by a 25% material ratio macroporous device 10, a reduction of 25% blood flow into the aneurysm sac is possible, with higher material ratios, for example 70-80%, or preferable 75%, even greater inhibition of blood flow to the aneurysm is achieved. It is expected that the percentage reduction in blood flow will exceed the simple percentage material ratio due to the viscosity of blood, as well as further reduction of blood flow due to flow disruption and dispersion. The geometry of the aneurysm can also play a role in the effectiveness and operation of the device.

Chemical Properties of the Membrane

The membrane is preferably made from biocompatible, highly elastomeric polymer. Polyether urethane (PEU) or polycarbonate urethane (PCU) may be used.

Trade names for PEU include Tecoflex, Tecothane, Hapflex, Cardiothane, Pellethane, and Biospan. Trade names for PCU include ChronoFlex, Carbothane, and Corethane.

In some embodiments the membrane is made from BioSpan F, a material developed by Polymer Technology Group (PTG), Berkeley, Calif., USA. BioSpan F is a polyurethane based material with fluorocarbon surface-modified end groups. In studies performed both in vitro and in vivo, this material has been shown to possess excellent compatibility properties matching the environment of small blood vessels. The selection of BioSpan F for the membrane of the device in treating small vessels is preferred due to resistance to thrombogenesis as compared with PET or e-PTFE membranes. Preferably, the membrane fashioned from BioSpan F will include a specific pore pattern as described earlier to obtain better resolution and healing of the aneurysm.

TABLE 4

Summary of Protein Adsorption Test

| Test article | Concentration of protein found (µg/ml) | Amount of protein (µg) | Adsorbed protein (µg/cm$^2$) | Adsorbed protein (µg/g) |
|---|---|---|---|---|
| BioSpan | 5.5 | 28 | 1.4 | 230 |
| BioSpan F | 3.5 | 18 | 0.88 | 160 |
| ePTFE | 16 | 80 | 4.0 | 4600 |

Figure 25A:
FIG. 25A is an image of a chronic angiograph of iliac arteries showing the patency of vessels implanted with the endovascular device having a solid membrane made from a polyurethane based material with fluorocarbon surface-modifying end groups.

Table 4 shows initial results from in vitro biocompatibility tests comparing three materials; BioSpan, BioSpan F, and ePTFE. As can be seen, BioSpan F was the least thrombogenic of the three. The results of animal studies, shown in FIGS. 25A and B, confirm the superior biocompatibility of BioSpan F. An endovascular device 76 with a membrane made from BioSpan F was placed in the right iliac artery 78 (left side of FIG. 25A). The angiographic study shows normal patency of the artery after healing of the implant. In contrast, an endovascular device 80, made from a different membrane material, and placed in the left iliac artery 74 of the same animal (right side of FIG. 25A), showed poor biocompatibility, such that after healing the vessel 74 became completely occluded in the region of the device 80.

Figure 25B:
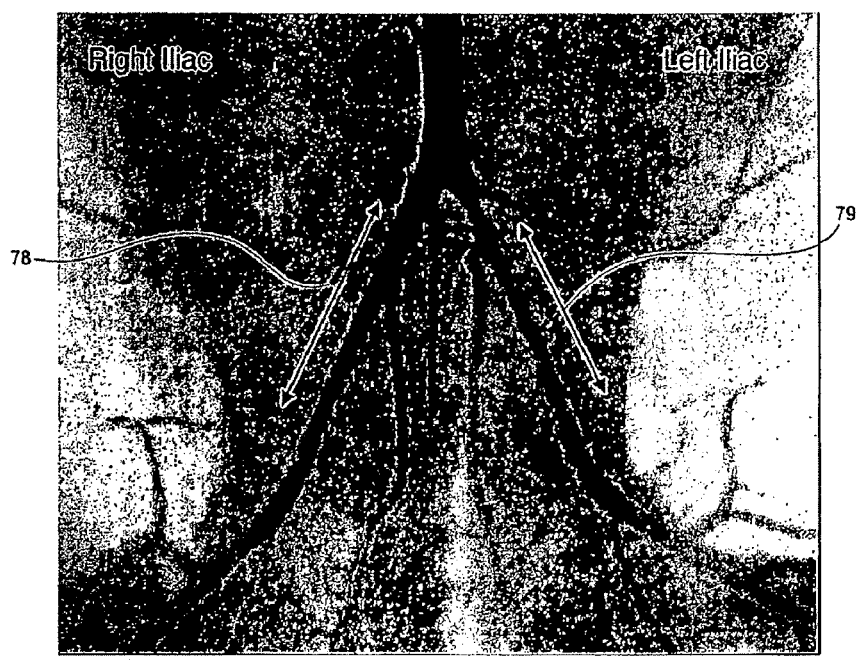
FIG. 25B is an image of a chronic angiograph of iliac arteries showing the patency of vessels implanted with the endovascular device having a porous membrane made from a polyurethane based material with fluorocarbon surface-modifying end groups.

Additional animal studies, shown in FIG. 25B, revealed that when BioSpan F was used as the membrane material, a stent covered with a porous membrane 78 had a lower degree of narrowing and thus had better healing properties than the stent covered with a solid membrane 79. With a porous membrane approximately 5% narrowing was observed (left side of FIG. 25B), while with a solid membrane 15-20% narrowing was seen (right side of FIG. 25B).

In some embodiments, membranes can be fashioned from materials of the BioSpan family using the same surface modifying end group technique, but with application of different end groups. BioSpan PS, for example, is a surface modified material with PEO and silicon end groups.

Membranes With Permanently-Attached Agents

Figure 26:
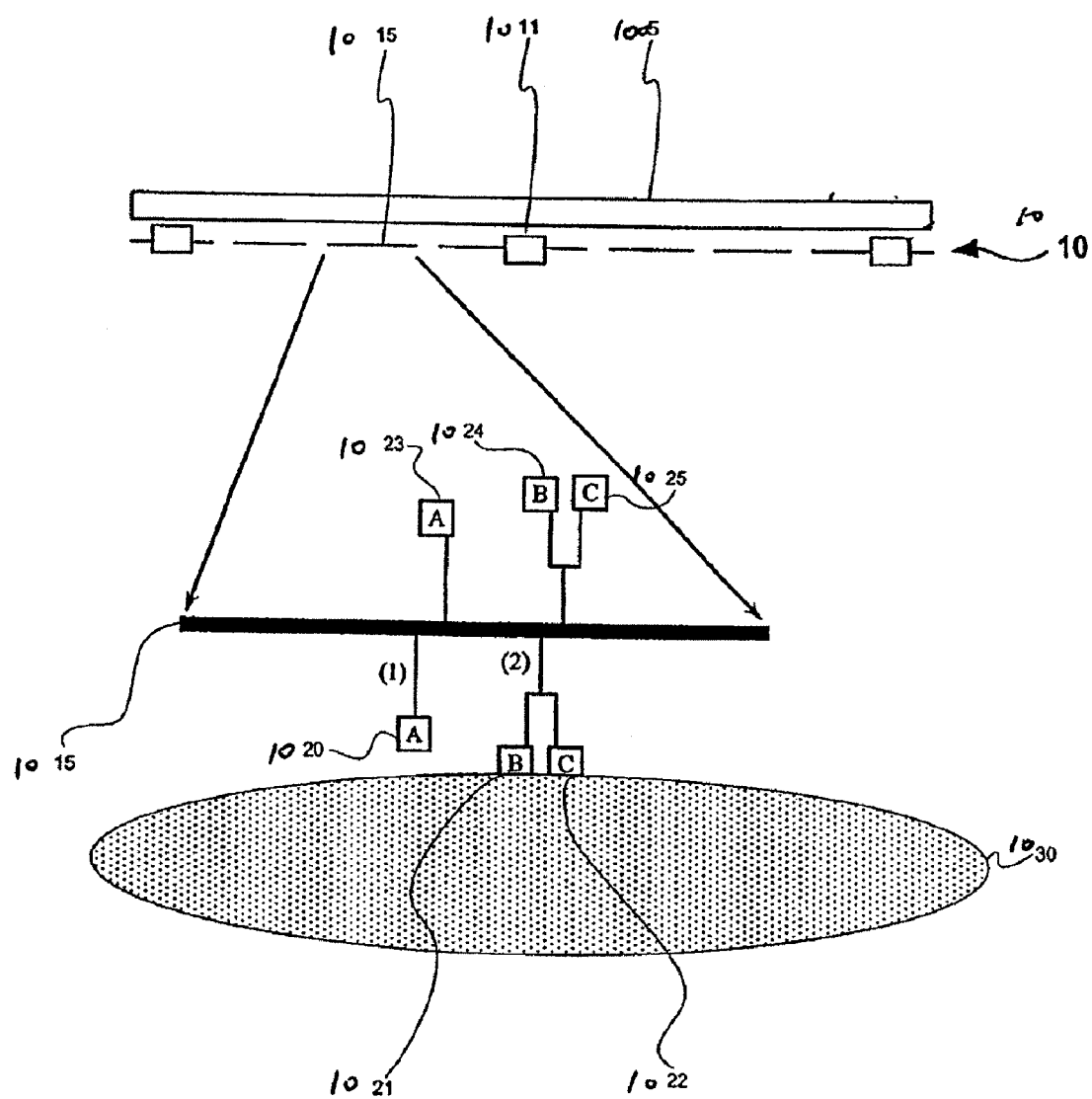
FIG. 26 illustrates an embodiment comprising a membrane having permanently attached agents.

In some embodiments, one of which is illustrated in FIG. 26, the device 1010 is a stent comprising struts 1011, covered by an ultra-thin membrane or coating 1015, and where the membrane 1015 is of substantially uniform porosity over its length. The membrane comprises two surfaces, a luminal surface and a vessel wall surface. On the luminal surface, agents 1020, 1021, 1022 are permanently attached to the membrane 1015. On the vessel wall surface, agents 1023, 1024, and 1025 are permanently attached to the membrane. At least one capture agent 1021 is permanently attached to the luminal surface of the membrane 1015 to capture a desired target component 1030 present in the fluid passing through the vessel. At least one signal agent 1022 is permanently attached to the luminal surface of the membrane 1015 to signal the captured target component 1030 to up regulate or down regulate a cell function of the captured target component 1030 to enhance endothelialization and healing.

The cell function being regulated can include, but is not limited to, proliferation, migration, maturation, and apoptosis. The desired target component 30 can include, but is not limited to, an endothelial progenitor cell, in which case the signal agent 22 could up regulate the rate of endothelialization, and reduce the time for inflammation and thrombosis. Conveniently it is possible to combine a membrane having uniform porosity, with one comprising agents, 1020, 1021, 1022, permanently attached to the membrane. A membrane configured in this way would thus be adapted to substantially prevent blood flow to an aneurysm, while maintaining blood flow to perforators, and in addition could provided various agents that would enhance the process of healing the aneurysm.

The pharmaceutical agents 1020, 1021. 1002, coated on the lumen side of the membrane 1015, prevent the occlusion of the original patent lumen. In some embodiments, the capture and agent 1021 is arranged in a first conformation of a single arm structure made of an organic linker anchored to the membrane 1015. The organic linker may be a short chain of organic molecules anchored on one end to the membrane 1015, and the other end bound to the agent molecule that captures specific endothelial cells from the blood to promote endothelialization. The capture and signal agents 1020, 1021, 1022 are arranged in a second conformation of a branched structure made up of an organic linker anchored to the membrane 1015. The capture agent 1021 specifically captures endothelial progenitor cells similar to the other capture agent 1020, while a signal agent 1022 enhances endothelial cell alignment and proliferation. Alternatively, the signal agent 1022 is arranged in a first conformation of a single arm structure made up of an organic linker anchored to the membrane 1015.

On the vessel wall side of the membrane 1015, a third pharmaceutical agent 1023 is permanently attached to the vessel wall surface of the membrane 1015 to enhance healing of the vessel wall 1005 from injury after the stent 1011 is deployed. Alternatively, the agents on the vessel wall side of the membrane 1015 also encourage proliferation of vessel wall components, for example, intima, elastic lamina, for enhancing the healing of the weakened, damaged or diseased portion of the vessel wall, for example, the aneurysm neck.

The agents can be effective to reduce, minimize, or prevent, immune reactions to foreign bodies. In some embodiments, agents can be effective to attract and capture endothelial cells, or endothelia progenitor cells, to aid in the formation of a healthy endothelium in the region of the aneurysm being treated. The lumen side of the membrane can be configured to generally discourage factors that are involved in thrombosis.

The capture and signal agents 1021, 1022, can include, but are not limited to, enzyme regulators tagged with antibodies or peptides, ceramides like L-PDMP, peptides, antibodies, naturally occurring molecules, and synthetic molecules, a nucleic acid, or even a polynucleotide, if desired. Specifically, the signal agent 1022 can be an endothelial cell specific L-PDMP or an smooth muscle cell-specific D-PDMP, that can bind specifically to target molecules on endothelial cells or progenitors. Peptide or antibodies have high binding affinity and specificity for endothelial cells and progenitors. Naturally occurring molecules (pure or synthesized) can mimic part of the basal lamina of the endothelium, so that endothelia cells or progenitors will preferentially bind and orient on the membrane. For example, laminin-mimetic pentapeptide immobilized on the lumen surface can be effective as a capture agent. The choice of capture agent is not considered to be a limitation of the disclosure. A number of molecules or moieties will be useful in preventing blood flow to an aneurysm, while maintaining flow to perforators, and which will promote healing and/or endothelialization, while reducing the risk of thrombosis or other injury to the vessel being treated are considered to be within the scope of the disclosure.

The signal agent 1022 can also be an anti-inflammatory agent in order to reduce recruitment and infiltration of white blood cells. Thus, through the choice of various signal agents it is possible to enhance attachment of endothelial cells to the membrane, while minimizing the inflammatory response. The capture agent 1021 and signal agent 1022 thus act cooperatively to increase the rate of endothelialization and decrease the during which thrombosis and restenosis might occur after the stent is expanded.

Figure 27:
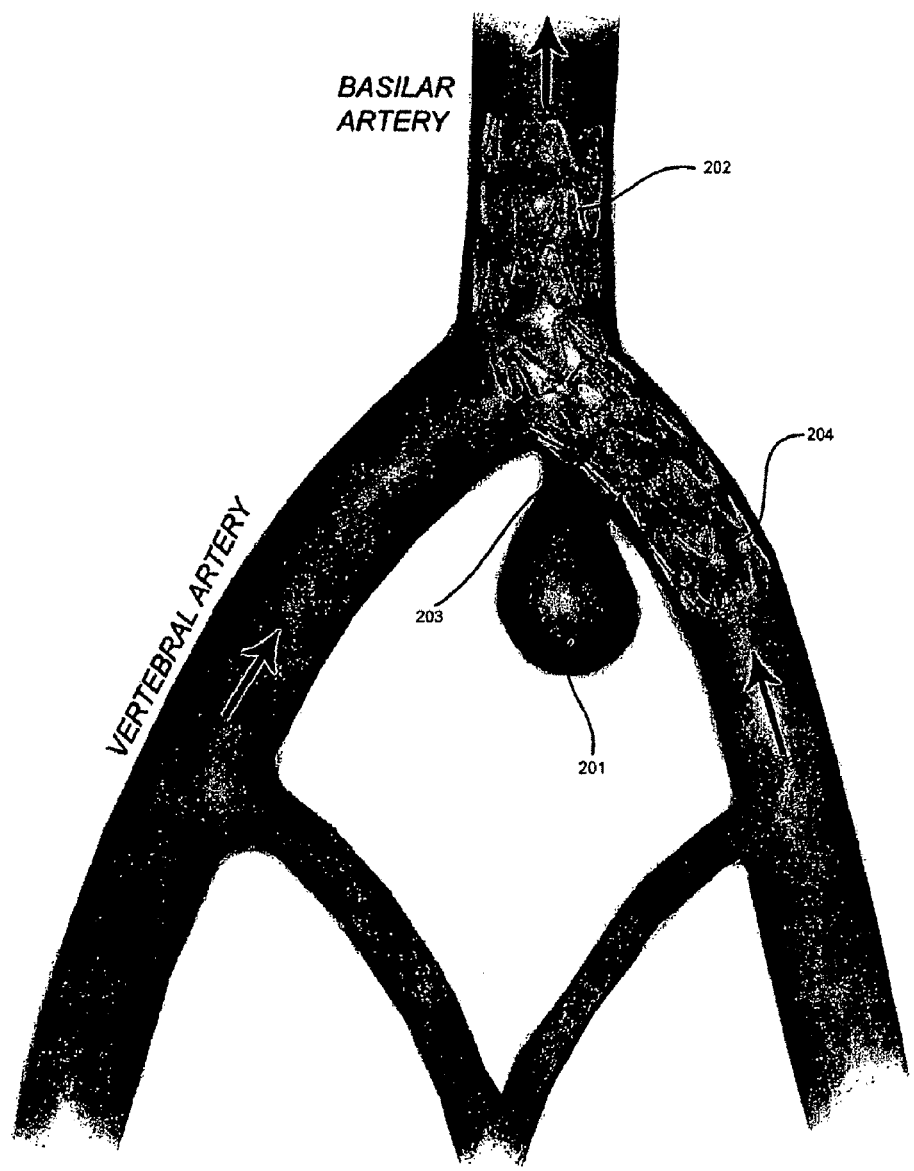
FIG. 27 is a diagrammatic view of a stent with a membrane being used to treat a bifurcation aneurysm in a first example.
Figure 28:
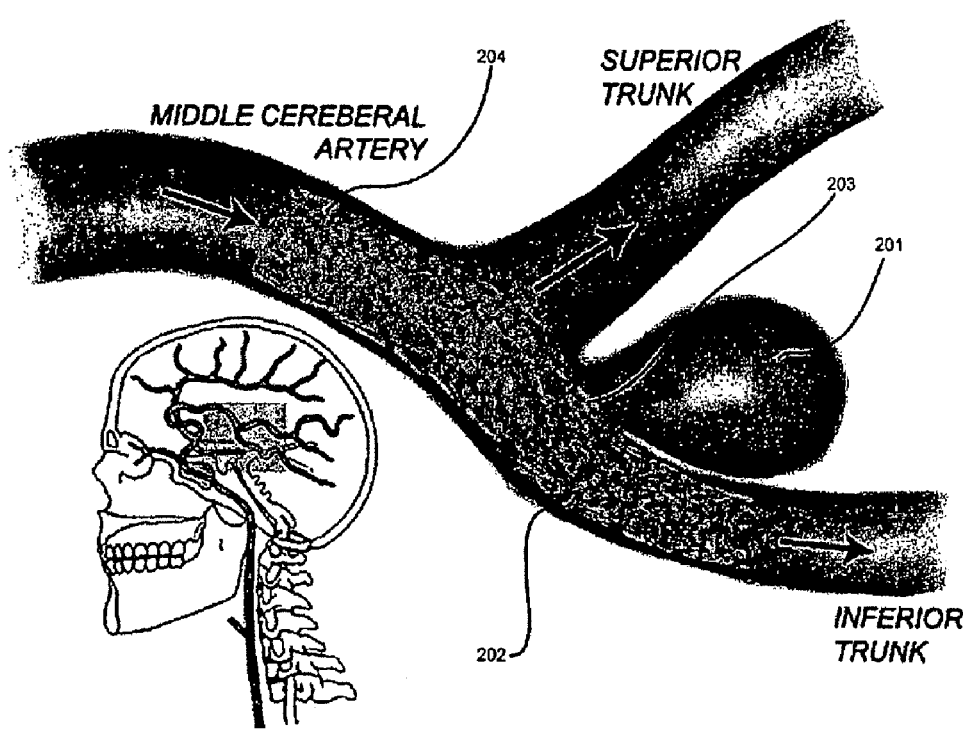
FIG. 28 is a diagrammatic view of a stent with a membrane being used to treat a bifurcation aneurysm in a second example.
Figure 29:
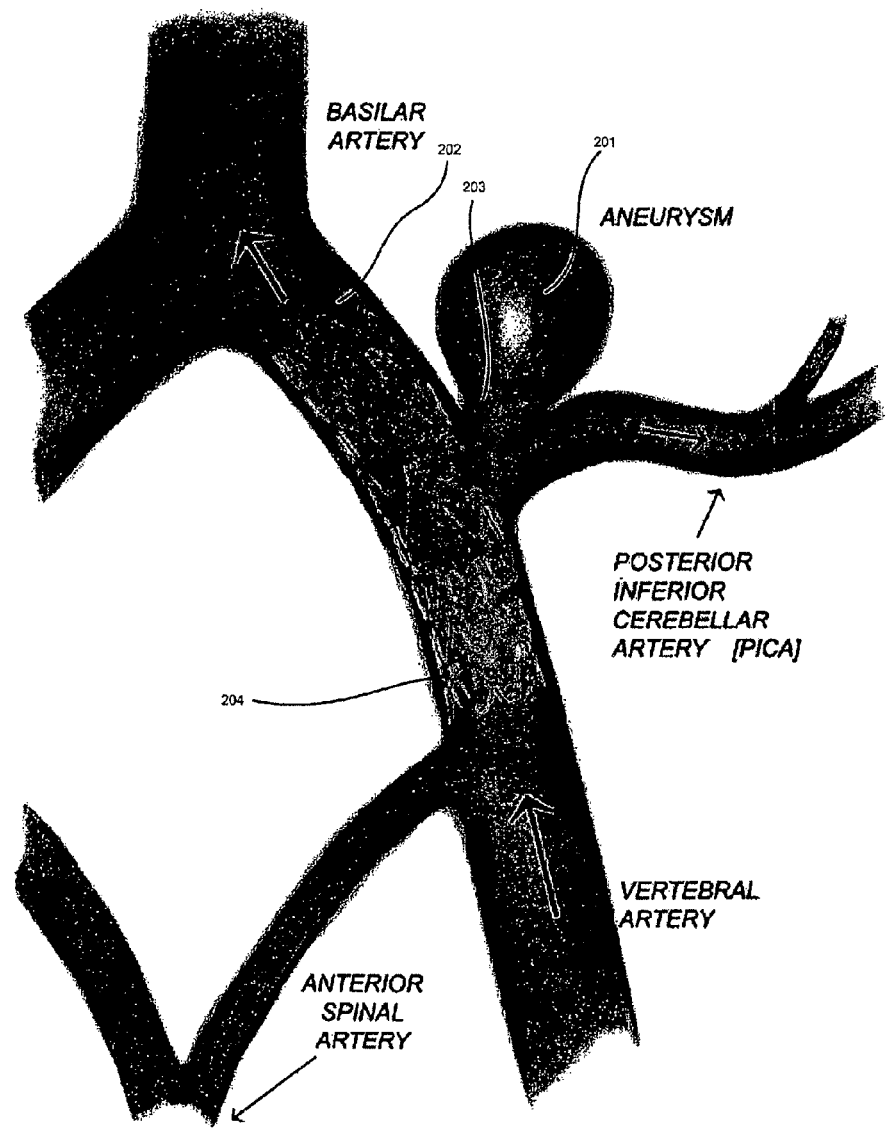
FIG. 29 is a diagrammatic view of a stent with a membrane being used to treat a bifurcation aneurysm in a third example.

As shown in FIGS. 27 through 29, in some embodiments the stent 202 can be used to treat a bifurcation or trifurcation aneurysm 201. It should be noted that the use of the device is not limited to those embodiments that are illustrated. The stent 202 is implanted to be partially located in a main artery extending to be partially located in a subordinate artery. For example, in FIG. 27, two vertebral arteries join to the basilar artery. The stent 202 is deployed such that it is located in the basilar artery and in a vertebral artery (right side) where the aneurysm 201 is formed. On the other vertebral artery (left side), blood continues to flow to the basilar artery without any obstruction since the membrane 203 is permeable to blood flow. Preferably, the membrane 203 covers the whole stent 202, and the permeability of the membrane 203 allows blood flow through the left vertebral artery (left side). Conveniently, radio-opaque markers 204 are provided in order to permit more accurate placement of the stent 202.

In FIG. 28, the middle cerebral artery divides into the superior trunk and the inferior trunk. The stent 202 is deployed such that it is located in the middle cerebral artery and in the inferior trunk. Again, the struts of the stent 202 do not inhibit blood flow to the superior trunk, and blood flows through the stent 202 to the inferior trunk.

In FIG. 29, the stent 202 is deployed in the vertebral artery. As the aneurysm 201 in this example is located in a middle portion of the vertebral artery, there is no need for the stent 202 to be located in more than one artery. When implanted, the stent 202 diverts blood flow away from the aneurysm 201. This leads to occlusion of the aneurysm 201 and keeps the arterial branches and the perforators patent. The stent 202 does not require precise positioning because it is uniformly covered with a porous membrane 203. Thus, most of the circumferential surface of the stent 202 is covered by the membrane 203, and thus the vessel wall will be uniformly contacted by the membrane in the area of the stent.

Due to the particular porosity and dimensions of the membrane 203, blood circulation to the aneurysm 201 is obstructed while blood supply to perforators and microscopic branches of main brain arteries as well as larger arteries is permitted. As described earlier, obstructing blood supply to the aneurysm 201 isolates the aneurysm 201 from normal blood circulation. The aneurysm in effect "dries out." The stent 202 and membrane 203 thus treats the aneurysm 201 by altering the hemodynamics in the aneurysm sac such that intra-aneurysmal thrombosis is initiated. At the same, blood flow into the arteries (branch, main, big or small) are not significantly affected by the implantation of the stent 202 or the membrane 203 due to the special porosity of the membrane 203. Although a bifurcation aneurysm has been described, it is envisaged that the stent 202 may be used to treat a trifurcation aneurysm, or other aneurysms, in a similar manner.

As used herein, the terms "secured to" and "coupled to" include direct and indirect means to secure and couple elements and/or components of endoprosthetic devices of the invention.

FIG. 30a illustrates an embodiment of a deployed endoprosthetic device 395. As shown, the distal assembly 400 of device 395 is made up of a plurality of engagement members 405, 410, 415, 420, coupled to flow-reducing member 425. While the embodiment illustrated in FIG. 30a comprises four engagement members 405, 410, 415, 420, some embodiments comprise one or more engagement members. Distal portions of the engagement members 405, 410, 415, 420 are curled and engage inner surfaces of an aneurysm 200. Flow reducing member 425 comprises a membrane 440, resides within the vessel 210, and reduces blood flow from the vessel 210 into the aneurysm 200. Device 395 can be delivered to the aneurysm by catheter 450 over a guide wire 452, and device 395 can be repositioned at or within the aneurysm 200, or entirely removed from the aneurysm as described herein.

In some embodiments, the delivery of an aneurysm occlusion device can be accomplished by advancing a guide wire through the vasculature and into the aneurysm, advancing a catheter over the guide wire, and withdrawing the guide wire. At this point, an aneurysm occlusion device can be advanced by a pusher, and pushed through the catheter until the device is positioned at least partially within the aneurysm (e.g. a neck of an aneurysm).

In some embodiments, the delivery of an aneurysm occlusion device can be achieved by a multilumenal catheter comprising a guide wire lumen and a pusher-device. The guidewire is advanced through the vasculature and into the aneurysm. The catheter is advanced through the vasculature and to the aneurysm by tracking over the guide wire, disposed within the guide wire lumen, with a pusher and a device loaded into the pusher-device lumen of the catheter. Upon deployment, the pusher can be used to advance the device into the aneurysm. In some embodiments, the pusher can be used to retract the initially advanced device so as to reposition the device within the aneurysm. In some embodiments, the device and the pusher can be reversibly coupled, and the device released from the pusher by breaking of a chemical bond and/or an electrical heating process.

In some embodiments, an aneurysm occlusion device can, alone or coupled with a catheter delivery device, have an outside diameter in a range of from about 0.017" to 0.035." In some embodiments, an aneurysm occlusion device can, alone or coupled with a catheter delivery device, have an outside diameter in a range of from about 0.022" to 0.030."

In some embodiments, the device comprises a balloon (e.g. a flow reducing member), which is inflated once the device has been delivered to the aneurysm, thereby expanding the distal assembly of the device. The expanded device is released from the catheter, and the catheter is withdrawn from the vasculature. The expanded device engages an inner surface of the aneurysm, which secures the device at the aneurysm in a position in which the flow reducing member(s) reduces blood flow from the vessel into the aneurysm.

In some embodiments, the device comprises shape-memory elements that, upon the device being released from the catheter, provide movement to the distal assembly so that it engages an inner surface of the aneurysm, thereby securing the device in a position in which the flow reducing member(s) reduce blood flow from the vessel into the aneurysm.

In some embodiments, the device comprises one or more forming elements, the manipulation of which provide(s) movement to the distal assembly into a position in which it engages an inner surface reduces blood flow from the vessel into the aneurysm.

In certain embodiments, the size of device is chosen such that, when in place at the aneurysm, it remains at least slightly elastically compressed, and therefore has a restoring force which facilitates secure positioning. In certain embodiments, a device in place at the aneurysm can rely on the restoring force of deformed tissue for secure positioning, and/or on hooks, barbs, or other independent fixation elements included as part of the device structure.

In FIG. 30a, Engagement members 405, 410, 415, 420 of device 395 can be made of metals or polymers, such as NiTi, tungsten, stainless steel, iridium, platinum alloy, polyurethane, polyethylene terephthalate, polyvinylchloride, nylon, polyimide, polyurethane ether, polyurethane ester, polyurethaneurea, polylactide, polyglycolide, poly-orthoester, polyposphazene, poly anhydride, and polyphosphoester. The engagement members 405, 410, 415, 420 can have shape-memory properties that enable self expansion from a first, delivery position to the illustrated second, deployment position. Engagement member 405, 410, 415, 420 movement from a first position to the illustrated second position can be accomplished by assisted movement of the engagement members, either in the absence of or in combination with any degree of shape-memory properties that engagement members 405, 410, 415, 420 may have. Assisted engagement member movement can be accomplished by, for instance, inflating a balloon located at a central axis of the distal assembly 400.

Flow reducing member 425 can comprise a porous or nonporous membrane 440, as described herein, and can be expandable from a first, delivery position to a second, deployed position, in which at least a portion of the membrane 440 of the flow reducing member 425 is adjacent to an inner surface of the vessel 210. Flow reducing member 425 can comprise a frame, inflatable balloon, and/or thick plug. Frames of flow reducing members can comprise polymers and/or metals, such as such as NiTi, tungsten, stainless steel, iridium, platinum alloy, polyurethane, polyethylene terephthalate, polyvinylchloride, nylon, polyimide, polyurethane ether, polyurethane ester, polyurethaneurea, polylactide, polyglycolide, poly-orthoester, polyposphazene, poly anhydride, and polyphosphoester, and comprise struts. Flow reducing members can be coupled to a distal assembly and/or each other by weld, interweaving, suture, stitch, adhesive, combinations thereof, etc.

FIG. 30b illustrates a cross sectional view of device 395 shown in FIG. 30.

FIG. 31 illustrates a device 495 similar to the one shown in FIG. 30, but the engagement members 405, 410, 415, 420 of device 495 illustrated in FIG. 31 are curled in a different manner than those of device 395 of illustrated in FIG. 30. In addition, device 495 illustrated in FIG. 31 comprises a linking member 435, whereas device 395 shown in FIG. 30 does not have a linking member.

Figure 32:
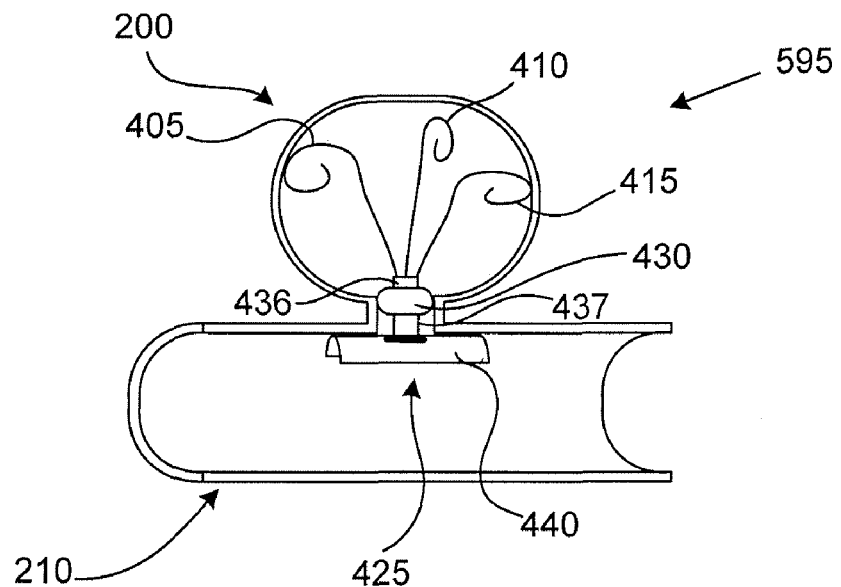
FIG. 32 illustrates an embodiment of a deployed device comprising a distal assembly, engagement members, a flow-reducing member comprising a membrane residing in the aneurysm, another flow-reducing member comprising a plug residing in the vessel, and two linking members.

FIG. 32 illustrates a device 595 similar to device 495 shown in FIG. 31, but device 595 illustrated in FIG. 32 comprises three engagement members 405, 410, 415, whereas device 495 shown in FIG. 31 comprises four engagement members 405, 410, 415, 420. Device 495 shown in FIG. 31 has one flow reducing member 425, whereas device 595 illustrated in FIG. 32 further comprises a second flow-reducing member 430 that comprises a balloon, resides in the aneurysm 200, and reduces blood flow from the vessel 210 into the aneurysm 200. In addition, device 595 illustrated in FIG. 32 further comprises two linking members 436 and 437 that couple flow reducing members 425, 430 to each other and to the distal assembly 400, whereas device 495 illustrated in FIG. 31 comprises one linking member. A linking member can couple, directly or indirectly, itself to another linking member, a flow reducing member, and/or a distal assembly.

Figure 33:
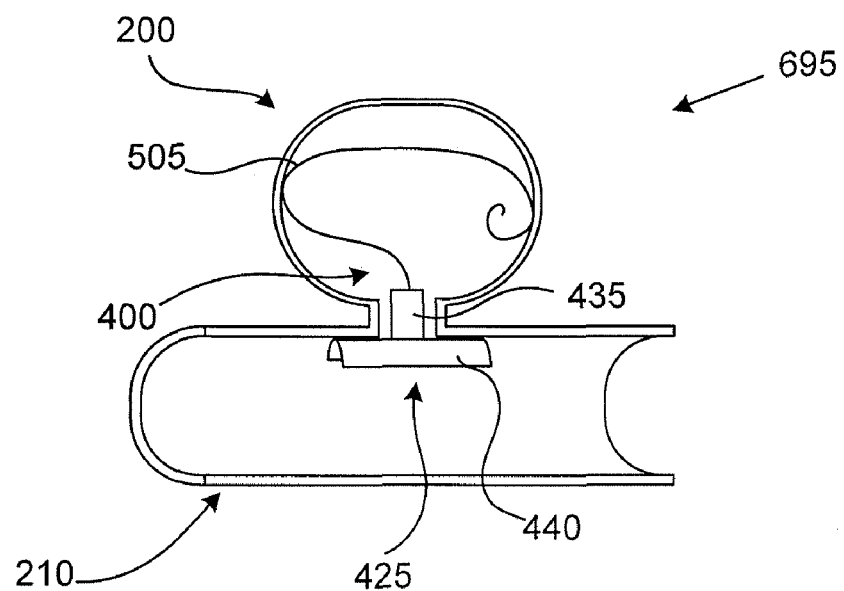
FIG. 33 illustrates an embodiment of a deployed device comprising a distal assembly, an engagement member comprising a curve, a flow-reducing member comprising a membrane, and a linking member.

FIG. 33 illustrates a device 695 similar to device 495 shown in FIG. 31, but device 695 illustrated in FIG. 33 has one engagement member 505, whereas device 595 shown in FIG. 32 has three engagement members. As can be seen in FIG. 33, first and second portions of engagement member 505 engage first and second regions of the inner wall of the aneurysm 200, and the first and second portions of the engagement member can be separated by a space of at least 2 mm.

Figure 34:
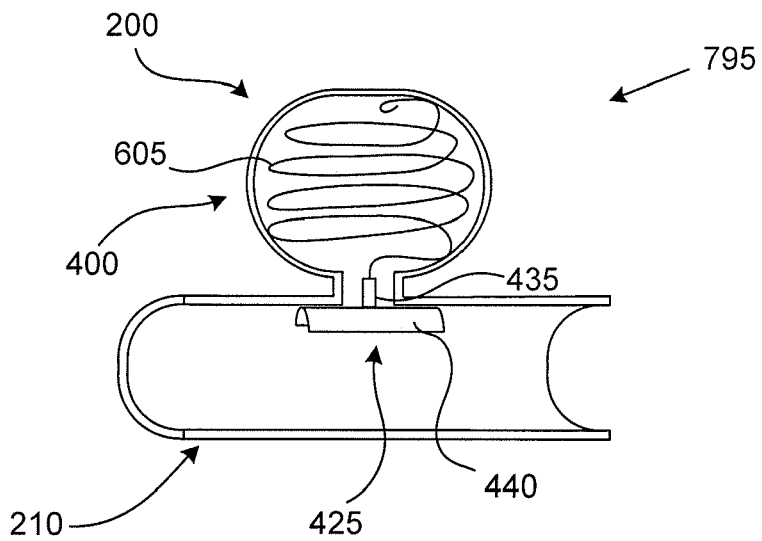
FIG. 34 illustrates an embodiment of a deployed device comprising a distal assembly, an engagement member comprising a helical shape, and a flow-reducing member residing in the vessel.

FIG. 34 illustrates a device 795 that comprises a flow reducing member 425 that comprises a membrane 440, a linking element 435, and a distal assembly 400 that engages an inner surface of an aneurysm in the illustrated, deployed position. The distal assembly is comprised of an engagement member 605 having a helical shape, first and second portions of which engage first and second regions of the inner wall of the aneurysm 200, and the first and second portions of the engagement member can be separated by a space of at least 2 mm.

Figure 35:
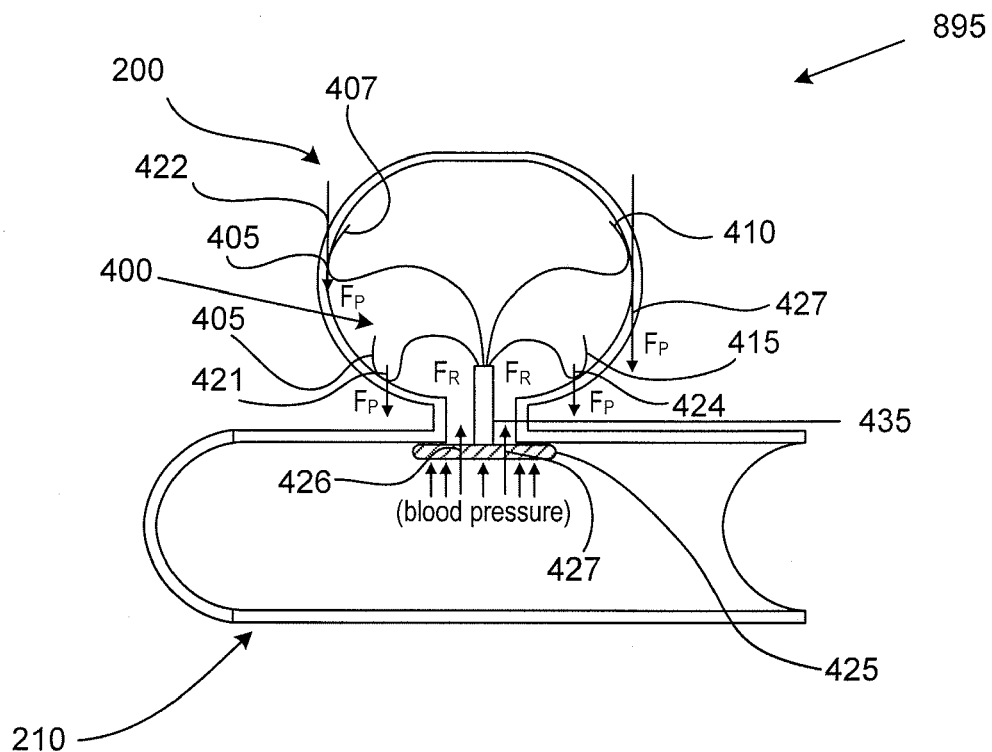
FIG. 35 illustrates an embodiment of a deployed device together with certain forces that contribute to the secured positioning of the deployed device.

FIG. 35 illustrates a device 895 that comprises a flow reducing member 425, positioned in the vessel 210 and comprising a membrane 440. The device 895 also comprises a distal assembly 400, within an aneurysm 200, having four engagement members 405, 407, 410, 415. Linking member 435 couples the flow reducing member 425 to the distal assembly 400. Also illustrated in FIG. 35 are some forces that contribute to securing the device 895 in the deployed position within the aneurysm. For example, pull forces (FP) 421, 422, 423, 424 are established by the engagement of engagement members 405, 407, 410, 415 with the inner surfaces of the aneurysm 200. In addition, resistance forces (RF) 426, 427 are established by the interaction between the flow reducing member and blood pressure of the vessel 210. The FPs 421, 422, 423, 424 and the RFs 426, 427 contribute to a secure deployment of the device 895.

It will be appreciated by persons skilled in the art that certain embodiments of the devices illustrated in FIGS. 30a-35, and variants of those devices, can be used in combination with knows aneurysm occlusion devices, such as aneurysm coils. In addition, such devices can be useful in the treatment of different types of aneurysms, such as intracranial aneurysms, saccular aneurysms, wide-neck aneurysms, fusiform aneurysms, bifurcation aneurysms, and trifurcation aneurysms.

It will be also appreciated by persons skilled in the art that numerous variations and/or modifications may be made to the specific embodiments disclosed herein, without departing from the scope or spirit of the disclosure as broadly described. The present embodiments are, therefore, to be considered in all respects illustrative and not restrictive of the invention, which is defined by the claims as presented herein.

What is claimed is:

1. An endovascular device, for treating an aneurysm of a body vessel, comprising:
   a distal assembly, movable from a first position to a second position when the distal assembly is at least partially in an aneurysm; and
   a first flow-reducing member, coupled to the distal assembly, that reduces blood flow from the body vessel into the aneurysm when the distal assembly is in the second position;
   wherein the distal assembly comprises a plurality of engagement members, each of which extends, from a proximal portion to a distal portion, away from the flow-reducing member;
   wherein, when the distal assembly is in the first position, each of the plurality of engagement members is substantially parallel to a central axis of the distal assembly;
   wherein, when the distal assembly changes from the first to the second position, the distal portion of each of the plurality of engagement members moves away from the central axis, such that the distal portions of each of the plurality of engagement members:
      substantially curl;
      move closer to the first flow-reducing member; and
      engage an inner surface of the aneurysm;
   the device further comprising a second flow-reducing member, coupled to the first flow-reducing member or to the distal assembly, that reduces blood flow from the body vessel into the aneurysm when the distal assembly is in the second position;
   the device further comprising a linking member that couples the second flow-reducing member to the first flow-reducing member or to the distal assembly;
   wherein the second flow-reducing member comprises a plug, and wherein, when the distal assembly is in the second position, the plug is configured to reside substantially within a neck of the aneurysm and substantially inhibits blood flow through the neck of the aneurysm.

2. The endovascular device of claim 1, wherein at least one of the plurality of engagement members comprises a polymer selected from the group consisting of ePTFE, polyurethane, polyethylene terephthalate, polyvinylchloride, nylon, polyimide, polyurethane ether, polyurethane ester, polyurethaneurea, polylactide, polyglycolide, poly-orthoester, polyphosphazene, polyanhydride, and polyphosphoester.

3. The endovascular device of claim 1, wherein at least one of the plurality of engagement members comprises a metal selected from the group consisting of NiTi, tungsten, stainless steel, iridium, and platinum.

4. The endovascular device of claim 1, wherein a distal end of at least one of the plurality of engagement members is blunt.

5. The endovascular device of claim 1, wherein, when the distal assembly is in the second position, a distal end of each of the plurality of engagement members engages the inner surface of the aneurysm.

6. The endovascular device of claim 1, wherein, when the distal assembly is in the second position, the first flow-reducing member is configured to reside in the body vessel.

7. The endovascular device of claim 1, wherein, when the distal assembly is in the second position, the first flow-reducing member is configured to reside in the aneurysm.

8. The endovascular device of claim 1, wherein, when the distal assembly is in the second position, the first flow-reducing member is configured to reside in the body vessel and the second flow-reducing member is configured to reside in the aneurysm.

9. The endovascular device of claim 1, wherein at least one of the linking member, the distal assembly, the first flow-reducing member, and the second flow- reducing member comprises at least one metal selected from the group consisting of NiTi, tungsten, stainless steel, iridium, and platinum.

10. The endovascular device of claim 1, wherein the linking member comprises a wire.

11. The endovascular device of claim 1, wherein each of the linking member, the first flow-reducing member, the second flow-reducing member, and the distal assembly comprises a metal, and wherein a weld couples the linking member to at least one of the distal assembly, the first flow-reducing member, and the second flow-reducing member.

12. The endovascular device of claim 1, wherein the first flow-reducing member comprises a membrane.

13. The endovascular device of claim 12, wherein the membrane comprises at least one polymer selected from the group consisting of ePTFE, polyurethane, polyethylene terephthalate, polyvinylchloride, nylon, polyimide, silicone, polyurethane ether, polyurethane ester, polyurethaneura, polylactide, polyglycolide, poly-orthoester, polyphosphazene, polyanhydride, and polyphosphoester.

14. The endovascular device of claim 12, wherein the first flow-reducing member is coupled to the distal assembly by suture or interweaving.

15. The endovascular device of claim 12, wherein at least a portion of the membrane is non-porous.

16. The endovascular device of claim 12, wherein the membrane comprises a porous section having a porosity over a length extending from a proximal end of the porous section to a distal end of the porous section;
   wherein a pore spacing and a pore size of the porous section determine the porosity of the porous section;
   wherein, when the distal assembly is in the second position, the membrane is effective to reduce blood flow into the aneurysm and to promote thrombosis at or in the aneurysm.

17. The endovascular device of claim 16, wherein the porosity is selected such that, when the distal assembly is in the second position, the porous section of the membrane is effective to enhance endothelial cell migration and tissue growth onto the membrane and to substantially inhibit blood flow from the body vessel into the aneurysm.

18. The endovascular device of claim 16, wherein a material ratio of the porous section of the membrane comprises a ratio of a total area of an outer surface of the porous section of the membrane that comprises material to a total area of an outer surface of the porous section that comprises pores.

19. The endovascular device of claim 12, further comprising at least one agent, permanently attached to the membrane, that, when the distal assembly is in the second position, promotes healing of the aneurysm.

20. The endovascular device of claim 19, wherein the at least one agent comprises at least one of a peptide, a protein, an enzyme regulator, an antibody, a naturally occurring molecule, a synthetic molecule, a nucleic acid, a polynucleotide, L-PDMP, and D-PDMP.

21. A method of treating an aneurysm of a body vessel comprising:
    providing an endovascular device comprising:
        a distal assembly, movable from a first position to a second position when the distal assembly is at least partially within an aneurysm, the distal assembly comprising a plurality of engagement members, each of which extends, from a proximal portion to a distal portion, away from the flow-reducing member and each of which, when the distal assembly is in the first position, is substantially parallel to a central axis of the distal assembly; and
        a first flow-reducing member, coupled to the distal assembly, that reduces blood flow from the body vessel into the aneurysm when the distal assembly is in the second position;
    positioning the distal assembly at least partially within the aneurysm; and
    changing the distal assembly from the first position to the second position such that the distal portion of each of the plurality of engagement members moves away from the central axis, whereby the distal portions of each of the plurality of engagement members:
        substantially curl;
        move closer to the first flow-reducing member; and
        engage an inner surface of the aneurysm;
    wherein the endovascular device further comprises a second flow-reducing member, coupled to the first flow-reducing member or to the distal assembly, that reduces blood flow from the body vessel into the aneurysm when the distal assembly is in the second position; and further comprising:
        positioning the second flow-reducing member at least partially in the aneurysm;
    wherein the endovascular device further comprises a linking member that couples the second flow-reducing member to the first flow-reducing member or to the distal assembly;
    wherein the second flow-reducing member comprises a plug, and wherein, when the distal assembly is in the second position, the plug is configured to reside substantially within a neck of the aneurysm and substantially inhibits blood flow through the neck of the aneurysm.

22. The method of claim 21, wherein at least one of the plurality of engagement members comprises a polymer selected from the group consisting of ePTFE polyurethane, polyethylene terephthalate, polyvinylchloride, nylon, polyimide, polyurethane ether, polyurethane ester, polyurethaneurea, polylactide, polyglycolide, poly-orthoester, polyphosphazene, polyanhydride, and polyphosphoester.

23. The method of claim 21, wherein at least one of the plurality of engagement members comprises at least one metal selected from the group consisting of NiTi, tungsten, stainless steel, iridium, and platinum.

24. The method of claim 21, wherein a distal end of at least one of the plurality of engagement members is blunt.

25. The method of claim 21, wherein, when the distal assembly is in the second position, a distal end of each of the plurality engagement members engages the inner surface of the aneurysm.

26. The method of claim 21, wherein, when the distal assembly is in the second position, the first flow-reducing member is configured to reside in the body vessel.

27. The method of claim 21, wherein, when the distal assembly is in the second position, the first flow-reducing member is configured to reside in the aneurysm.

28. The method of claim 21, wherein, when the distal assembl, is in the second position, the first flow-reducing member is configured to reside in the body vessel and the second flow-reducing member is configured to reside in the aneurysm.

29. The method of claim 21, wherein the first flow-reducing member comprises a membrane.

30. An endovascular device, for treating an aneurysm of a body vessel, comprising:
    a distal assembly, movable from a first position to a second position when the distal assembly is at least partially in an aneurysm; and
    a first flow-reducing member, coupled to the distal assembly, that reduces blood flow from the body vessel into the aneurysm when the distal assembly is in the second position;
    wherein the distal assembly comprises a plurality of engagement members, each of which extends, from a proximal portion to a distal portion, away from the flow-reducing member;
    wherein, when the distal assembly is in the first position, each of the plurality of engagement members is substantially parallel to a central axis of the distal assembly;
    wherein, when the distal assembly changes from the first to the second position, the distal portion of each of the plurality of engagement members moves away from the central axis, such that the distal portions of each of the plurality of engagement members:
        substantially curl;
        move closer to the first flow-reducing member; and
        engage an inner surface of the aneurysm;
    the device further comprising a second flow-reducing member, coupled to the first flow-reducing member or to the distal assembly, that reduces blood flow from the body vessel into the aneurysm when the distal assembly is in the second position;
    the device further comprising a linking member that couples the second flow-reducing member to the first flow-reducing member or to the distal assembly;
    wherein the second flow-reducing member comprises a plug, and wherein, when the distal assembly is in the second position, the plug is configured to reside substantially within a neck of the aneurysm and substantially inhibits blood flow through the neck of the aneurysm;
    wherein the plug comprises a balloon.

31. The endovascular device of claim 30, wherein at least one of the plurality of engagement members comprises a polymer selected from the group consisting of ePTFE, polyurethane, polyethylene terephthalate, polyvinylchloride, nylon, polyimide, polyurethane ether, polyurethane ester, polyurethaneurea, polylactide, polyglycolide, poly-orthoester, polyphosphazene, polyanhydride, and polyphosphoester.

32. The endovascular device of claim 30, wherein at least one of the plurality of engagement members comprises a metal selected from the group consisting of NiTi, tungsten, stainless steel, iridium, and platinum.

33. The endovascular device of claim 30, wherein a distal end of at least one of the plurality of engagement members is blunt.

34. The endovascular device of claim 30, wherein, when the distal assembly is in the second position, a distal end of each of the plurality of engagement members engages the inner surface of the aneurysm.

35. The endovascular device of claim 30, wherein, when the distal assembly is in the second position, the first flow-reducing member is configured to reside in the body vessel.

36. The endovascular device of claim 30, wherein, when the distal assembly is in the second position, the first flow-reducing member is configured to reside in the aneurysm.

37. The endovascular device of claim 30, wherein, when the distal assembly is in the second position, the first flow-reducing member is configured to reside in the body vessel and the second flow-reducing member is configured to reside in the aneurysm.

38. The endovascular device of claim 30, wherein at least one of the linking member, the distal assembly, the first flow-reducing member, and the second flow-reducing member comprises at least one metal selected from the group consisting of NiTi, tungsten, stainless steel, iridium, and platinum.

39. The endovascular device of claim 30, wherein the linking member comprises a wire.

40. The endovascular device of claim 30, wherein each of the linking member, the first flow-reducing member, the second flow-reducing member, and the distal assembly comprises a metal, and wherein a weld couples the linking member to at least one of the distal assembly, the first flow-reducing member, and the second flow-reducing member.

41. The endovascular device of claim 30, wherein the first flow-reducing member comprises a membrane.

42. The endovascular device of claim 41, wherein the membrane comprises at least one polymer selected from the group consisting of ePTFE, polyurethane, polyethylene terephthalate, polyvinylchloride, nylon, polyimide, silicone, polyurethane ether, polyurethane ester, polyurethaneura, polylactide, polyglycolide, poly-orthoester, polyphosphazene, polyanhydride, and polyphosphoester.

43. The endovascular device of claim 41, wherein the first flow-reducing member is coupled to the distal assembly by suture or interweaving.

44. The endovascular device of claim 41, wherein at least a portion of the membrane is non-porous.

45. The endovascular device of claim 41, wherein the membrane comprises a porous section having a porosity over a length extending from a proximal end of the porous section to a distal end of the porous section;
   wherein a pore spacing and a pore size of the porous section determine the porosity of the porous section;
   wherein, when the distal assembly is in the second position, the membrane is effective to reduce blood flow into the aneurysm and to promote thrombosis at or in the aneurysm.

46. The endovascular device of claim 45, wherein the porosity is selected such that, when the distal assembly is in the second position, the porous section of the membrane is effective to enhance endothelial cell migration and tissue growth onto the membrane and to substantially inhibit blood flow from the body vessel into the aneurysm.

47. The endovascular device of claim 46, wherein a material ratio of the porous section of the membrane comprises a ratio of a total area of an outer surface of the porous section of the membrane that comprises material to a total area of an outer surface of the porous section that comprises pores.

48. The endovascular device of claim 41, further comprising at least one agent, permanently attached to the membrane, that, when the distal assembly is in the second position, promotes healing of the aneurysm.

49. The endovascular device of claim 48, wherein the at least one agent comprises at least one of a peptide, a protein, an enzyme regulator, an antibody, a naturally occurring molecule, a synthetic molecule, a nucleic acid, a polynucleotide, L-PDMP, and D-PDMP.

* * * * *